United States Patent
Jacobs et al.

(10) Patent No.: US 8,170,830 B2
(45) Date of Patent: May 1, 2012

(54) METHOD AND SYSTEM FOR PROVIDING TOLERANCE TO INTERFERENCE AND OBSTRUCTIONS OF LINE OF SIGHT

(76) Inventors: James P. Jacobs, Littleton, MA (US); Mark Robert Schneider, Williston, VT (US)

(*) Notice: Subject to any disclaimer, the term of this patent is extended or adjusted under 35 U.S.C. 154(b) by 590 days.

(21) Appl. No.: 12/438,027

(22) PCT Filed: Aug. 22, 2007

(86) PCT No.: PCT/US2007/076475
§ 371 (c)(1),
(2), (4) Date: Feb. 19, 2009

(87) PCT Pub. No.: WO2008/024815
PCT Pub. Date: Feb. 28, 2008

(65) Prior Publication Data
US 2010/0241392 A1    Sep. 23, 2010

Related U.S. Application Data

(60) Provisional application No. 60/823,116, filed on Aug. 22, 2006, provisional application No. 60/823,113, filed on Aug. 22, 2006.

(51) Int. Cl.
*G06F 11/00* (2006.01)
(52) U.S. Cl. ........................ 702/150; 700/245
(58) Field of Classification Search ............... 702/150, 702/182–185, 188; 600/245, 258, 262
See application file for complete search history.

(56) References Cited

U.S. PATENT DOCUMENTS

| | | | |
|---|---|---|---|
| 5,909,649 A | 6/1999 | Saunders | 455/450 |
| 5,963,509 A | 10/1999 | Lindmuller et al. | 367/102 |
| 6,369,754 B1 * | 4/2002 | Levanon | 342/357.2 |
| 7,076,259 B2 | 7/2006 | Belcea | 455/456.1 |
| 7,315,274 B2 | 1/2008 | Fossum | 342/44 |
| 2005/0190098 A1 | 9/2005 | Bridgelall et al. | 342/118 |
| 2006/0061469 A1 | 3/2006 | Jaeger et al. | 340/539.13 |
| 2006/0158370 A1 | 7/2006 | Karashima et al. | 342/118 |
| 2006/0267764 A1 | 11/2006 | Morinaga et al. | 340/545.3 |
| 2007/0109177 A1 | 5/2007 | Baath et al. | 342/124 |
| 2008/0231501 A1 | 9/2008 | Isaji | 342/195 |
| 2010/0168764 A1 | 7/2010 | Jacobs | 606/130 |
| 2010/0231410 A1 | 9/2010 | Seisenberger et al. | 340/825.49 |

FOREIGN PATENT DOCUMENTS

| | | |
|---|---|---|
| EP | 1783517 | 5/2007 |
| WO | WO 2007085517 | 8/2007 |

OTHER PUBLICATIONS

Office action received in related case U.S. Appl. No. 12/438,043.

* cited by examiner

*Primary Examiner* — Edward Raymond

(57) ABSTRACT

Various aspects of the present invention are shown and described, each of which has stand alone utility in a navigated medical environment. A receiver position calibration system and method facilitates calibration of a reference frame prior to each navigated procedure. A concept and application of confidence weights is introduced. Confidence weights can be applied to distance calculations to mitigate the effects of interference and increase the tolerance of the navigated medical system. Multi-path interference is minimized through the transmission of a signal having a pattern of unique frequencies and filtering of the distance calculations for each frequency to identify the "best" distance in the presence of multi-path interference. A position determination method and system that transmits a signal having multiple frequency components permits positions to be identified with high resolution over a large area.

20 Claims, 20 Drawing Sheets

METHOD AND SYSTEM FOR PROVIDING TOLERANCE TO INTERFERENCE AND OBSTRUCTIONS OF LINE OF SIGHT

RELATED APPLICATIONS

This application claims priority under 35 U.S.C. §1.119(e) to provisional patent application Ser. Nos. 60/823,116 and 60/823,113 filed Aug. 22, 2006, incorporated herein by reference.

FIELD OF THE INVENTION

This invention relates to generally to the field of navigated surgery and more particularly to wireless tracking of objects with very fine precision.

BACKGROUND OF THE INVENTION

There are many applications in which radio frequency (RF) or microwave signals are used for tracking objects, such as Global Positioning Systems (GPS), Loran, aircraft navigation, military radar, and video motion capture. All of these use some sort of scheme for detecting the transit times or phases of the RF or microwave signals, followed by a processing or computational subsystem to determine the position and other parameters of the object being tracked.

In some of these applications, such as GPS, Loran, and aircraft navigation systems, the computational intelligence is mounted on the moving object, and the goal is for the operator of the object to determine its own position relative to the surrounding environment. In other applications, the processing capability is attached to the environment, and the goal is for people or systems to track multiple objects as they traverse through the environment.

For example, during navigated medical procedures such as Navigated Surgery (NS) and Image Guided Surgery (IGS) surgeons use electronic surgical instrument tracking to accurately track in real time where the instruments are relative to the patient anatomy during the operation. By combining computers and wireless instruments, navigated surgery systems give surgeons far more accuracy than ever before. During navigated medical procedures, transmitters are mounted on surgical instruments and on bone markers that are attached to a patient's anatomy. Receivers, distributed throughout the operating room, receive signals from the transmitters and use the signals to track instrument position relative to patient anatomy. A graphical interface may be used to display the relative positions of transmitting signals and anatomical markers to enable the surgeon to perform precise medical procedures. Alternatively, a computational model of the patient anatomy and the positions and orientations of the instruments may be used to guide robotic procedures.

Because distances in the medical environment are small and precision requirements are high, methods based on time differences of arrival of signals are not within the state of the art of current electronic technology. For example in an operating room, the positions of a patient's anatomy and of the surgical instruments must be known to a resolution of less than one millimeter (1 mm) in order for computer-assisted or navigated surgery to be viable. Since light travels 1 mm in approximately $3 \times 10^{-12}$ seconds, times would have to be measured accurately and repeatably in fractions of picoseconds, something that is beyond the scope of current electronic technology.

An alternative method is to measure the angles between the phases of a transmitted signal as it is received at different receiving antennas. It is possible to measure phase differences with a precision of about 1 percent. Therefore, if the wavelength of a transmitted signal is about 50 mm (i.e., a frequency of about 5.7 GHz), a phase difference of 1 percent translates to a positional precision of about 0.5 mm, which corresponds to a desired precision of navigated medical procedures.

Methods based on time measurements have a relatively simple calculation—d=c*t, where d is the distance between the transmitting and receiving antenna, c is the speed of light in air, and t is the travel time of the transmitted signal. In systems and methods based on phase differences, the computation is more complex. The phase of the received signal must be compared with the phase of a reference signal. The difference in these two phases can be converted into a linear measure, but this is not sufficient to give an absolute distance between the two antennas.

In particular, suppose that $\phi_1$ is the phase angle of the received signal (relative to the reference signal) when the transmitting antenna and receiving antenna are distance $d_1$ apart, and suppose that $\phi_2$ is the phase angle of the received signal (relative to the reference signal) when those same two antennas are distance $d_2$ apart. Then the difference in the two distances is given by $$(d_1 - d_2) = \frac{1}{2\pi f}(\phi_1 - \phi_2 + 2\pi k_{1,2}) \quad (eq\ 1)$$

where f is the frequency of transmission, the angles $\phi_1$ and $\phi_2$ are measured in radians, and $k_{1,2}$ is an integer representing the whole number of wavelengths in the difference $(d_1-d_2)$. There are many ways of determining $k_{1,2}$, including some innovative ways that are adapted to particular applications. Likewise, $\phi_1$ and $\phi_2$ can be known relative to a reference signal, but the absolute phases of $\phi_1$ and $\phi_2$ are dependent upon the phase delays in the electronics of the transmitter, receiver, and cables. In some applications, particularly medical applications where high precision is required, it is not possible to know these phase delays. As a result, it is also not possible to know a distance such as $d_1$ absolutely, but only relative to some other previously known distance, such as $d_2$.

Therefore, in medical applications (and some other applications), an object must be calibrated by first placing it at a known, fixed location in a frame of reference to determine the phase difference at that location. The object can then be tracked by noting the change in a received phase angle and converting this by Equation 1 to a change in distance from the known, fixed location.

The step of placing the object at the known location is called the object calibration process (or instrument calibration process). For example, in some navigated procedures, each instrument must be inserted into a calibration socket prior to usage, and possibly at times during the procedure. During the object calibration process, signals are transmitted between each antenna on the object and each antenna in that frame of reference. The differences between the phase angles of the received signals and the reference signals are measured and recorded. Collectively, these recorded phase differences are called the phase reference at the origin for that object. All other phase differences (between transmitted signals and reference signals) are then compared with the phase reference at the origin in order to determine how far each antenna has moved since object calibration.

For the purposes of this application, a frame of reference is a three-dimensional geometric coordinate system with respect to which motion is observed and with respect to which measurements are made. It will be appreciated that different applications may have different frames of reference. A typical frame of reference is the operating room in which a navigated medical procedure is performed. However, other applications may use a frame of reference attached to a particular part of the patient anatomy, and still others may associate it with a robotic tool.

Following the calibration, the motion of the object can be tracked by repeatedly measuring the changes in the phase angles between the reference signal and the signals detected by each receiver. In a typical installation, the phase angles are measured periodically at intervals of a small fraction of one second. Provided that the object does not move more than one wavelength during any interval, the change in the phase angle observed by a transmitting antenna and a receiving antenna can be converted into a change in distance between those two antennas. By knowing the changes in the distances between all of the transmitting and receiving antennas and by knowing the positions of the antennas on the moving object, the position of that object relative to its point of calibration can be determined with a desired degree of precision.

In US Patent Application 2006/0066485, Min teaches a system of transmitters and receivers that can detect phase differences of the required precision.

In theory, the change in the position of the object in three-dimensional space can be determined from the changes in the phases of the signal received by three receivers. However, in practical systems, there are a multiplicity of problems and challenges. Among them are:— a). While three receivers are theoretically sufficient to precisely locate the position of an object in three-dimensional space, and more receivers would be redundant. In practice, different combinations of three receivers determine different positions for an object, due to many possible factors. For example, a receiver may temporarily obstructed from line of sight to the object, the electromagnetic field of the RF waves may be distorted by metal objects or other interference, or the electronics of one receiver may not be as sensitive as another.

b). The relative positions of the antennas are not typically known within a fraction of a wavelength. In practical environments, some antennas may be many wavelengths apart. For example, in an operating room, an array of receiving antennas may be placed 2 meters above the patient (i.e., about 40 wavelengths) and the array itself may be 2 meters in diameter. In some situations, the receiver array may be on a portable cart that is wheeled into position prior to a surgical operation. Therefore, some method of calibrating the antennas in the frame of reference is needed before the positions of any objects can be determined.

c). Radio and microwave signals are subject to "multipath" distortion. That is, a transmitted signal may take multiple paths to the receiver. It is difficult with these methods to differentiate the straight line signal from the interference of signals taking other paths. Methods are needed for filtering out this distortion or for using redundant information to accurately discriminate the positions of objects.

d) In practical applications, one or more receivers may "lose sight" of an object. For example, a person or another object may temporarily get between a transmitter and a receiver, or the object may be dropped, or a transmitted signal may be corrupted or badly distorted. In all of these cases, the continuous tracking of an object from one update cycle to another is lost, and the absolute position of the object becomes ambiguous. Methods are needed to recover the positions of objects lost in this way.

e) A typical application environment will have multiple objects, each with multiple transmitters. In many situations, not only must the position of each object be known but also its orientation. If the geometry of an object is known exactly, it requires at least three antennas on the object to determine its orientation. However, if any signal from any one of those antennas is distorted or blocked, the orientation is lost. Methods are needed to maintain accurate position and orientation information about all of the objects in the field of interest.

f) Some application environments require very frequent updating of position and orientation information. For example, in robotic assisted surgery, all instruments and anatomic markers must refresh position information with frequencies up to 1 kilohertz (1 KHz) or more. Methods are needed that allow such frequent updating.

It would be desirable to determine a system and method that would provide the precise location and orientation of multiple objects with precisions of a small fraction of the wavelengths of the transmitted signals at a frequency that would support robotic assisted surgery.

SUMMARY OF THE INVENTION

According to one aspect of the invention, a method for determining a position of an object includes the steps of generating a confidence weight for association with a measured distance between the object and an antenna in response to historical data associated with the antenna and determining a position of the object including applying the confidence weight to the measured distance to control a degree of contribution of the measured distance in a determination of the position.

According to another aspect of the invention, A method of determining a position of an object includes the steps of, for each of a plurality of antennas: receiving a signal transmitted between the object and a respective antenna, generating a respective confidence weight to associate with a measured distance between the object and the respective antenna using historical information associated with at least one antenna of the plurality of antennas, comparing an estimated distance to each of the measured distances to generate a distance offset, applying the respective confidence weight to a function of the associated distance offset for each of the plurality of receivers to provide a plurality of weighted distance offsets, summing the weighted distance offsets and comparing a result to a threshold and responsive to the distance offset exceeding the threshold, adjusting the estimated distance and repeating the steps of comparing, applying and summing until the result is less than or equal to the threshold.

According to a further aspect of the invention, A system for determining the position of an object includes a computer readable medium accessible by a processor of the system, a historical data store stored on the computer readable medium and comprising historical information associated with an antenna, program code stored on the computer readable medium, for generating a confidence weight and associating the confidence weight with a measured distance between the antenna and the object; and program code stored on the computer readable medium for determining a position of the object including applying the confidence weight to the measured distance to control a degree of contribution of the measured distance to the position.

According to another aspect of the invention, a system for determining a position of an object includes a signal generator for generating a signal for transmission between the object and a plurality of antennas in a frame of reference, means for determining and associating a plurality of confidence weights to a corresponding plurality of measured distances, each measured distance associated with one antenna of the plurality of antennas, and positioning logic for determining a position of the object by deriving an estimated distance to each of the plurality of antennas using an estimated position, calculating a distance offset for each antenna by comparing the measured distance of the associated antenna to the associated derived distance, applying the confidence weights to a function of corresponding distance offsets to provide a plurality of weighted distance offsets and summing the weighted distance offsets to provide a result and responsive to the result being outside a threshold, adjusting the estimated position and repeating the steps of deriving, calculating and applying until the result is within the threshold.

DETAILED DESCRIPTION

Figure 1:
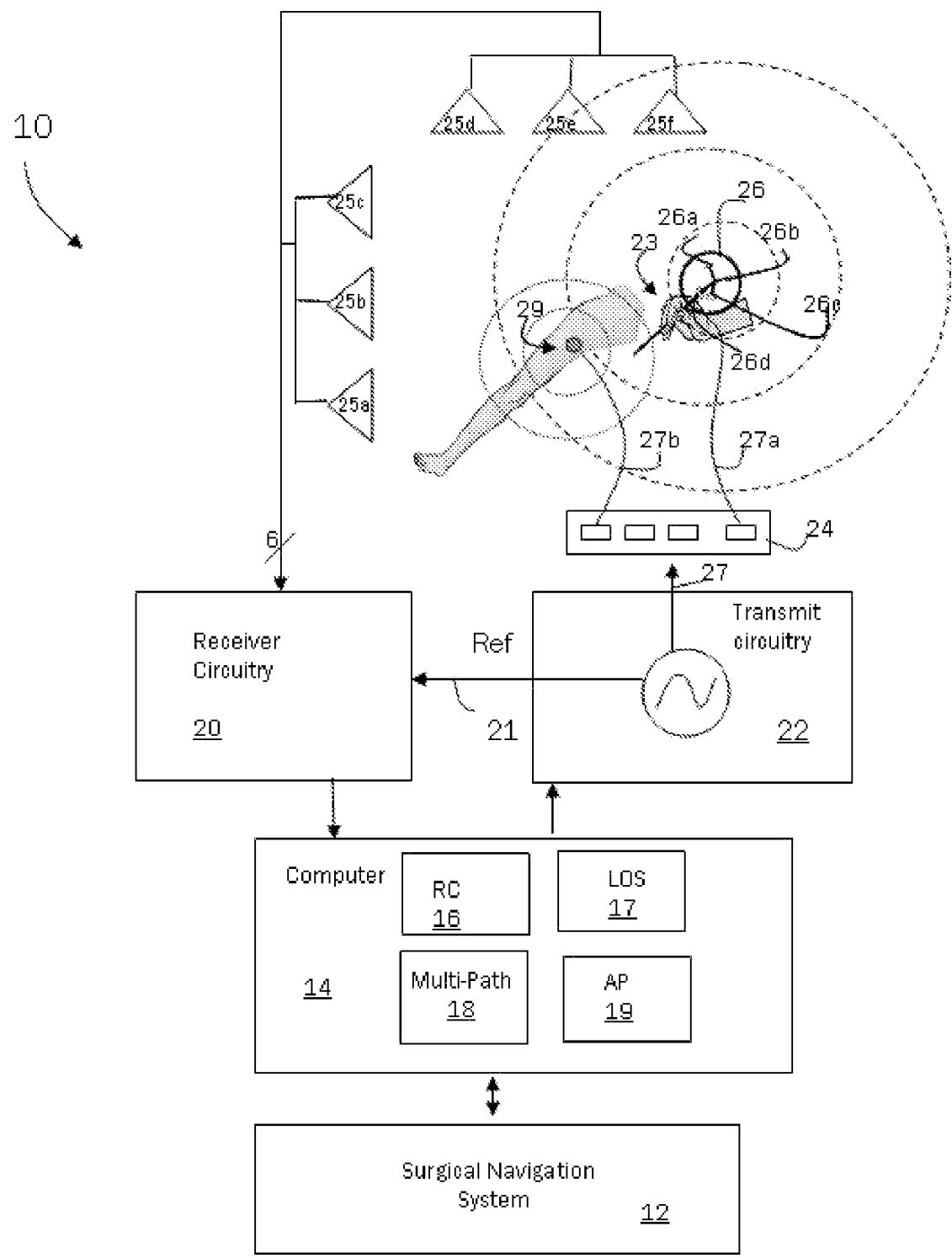
FIG. 1 is a block diagram illustrating exemplary components that may be included in a navigated medical environment incorporating the invention.

FIG. 1 illustrates several components that may be included in an exemplary embodiment of a navigated medical environment 10 in which various aspects of the present invention may advantageously be used to increase precision of instrument position calculations. As will be described in more detail below, instrument precision can be increased by performing any one of receiver calibration, alleviation of multipath effects, the provision of tolerance for line of sight obstruction and the resolution of absolute position.

In FIG. 1 a surgical navigation system 12 is coupled to a computer 14 which includes processing logic and a computer readable medium storing program code for use by the navigation system. As will be described in more detail below, the program code may include any one of the program codes illustrated in FIG. 1, including absolute positioning code module 16, multipath code module 17, line of sight tolerance code module 18 and receiver calibration code module 19. It should be noted that although four program codes are shown in FIG. 1, it is not a requirement that all four modules be provided in a navigated medical system; rather it can be appreciated that there are benefits to any system that incorporates any one of the modules. Accordingly, the present invention is not limited to inclusion of any particular program code module.

The computer 14 is coupled to transmit circuitry 22. The transmit circuitry 22 provides a signal 27 via distribution block 24 and lead 27a to transmit antenna assembly 26 (comprising antennas 26a-26d) that is mounted on a surgical instrument 23. The signal 27 may also be provided (via lead 27b) to transmit antennas on one or more anatomical markers (such as bone marker 29) that are rigidly fastened to the patient anatomy, wherein the anatomical marker also includes multiple transmit antennas, although they are not shown in FIG. 1 in detail. Finally, reference signal 21 is coupled to receiver circuitry 20.

Figure 2A:
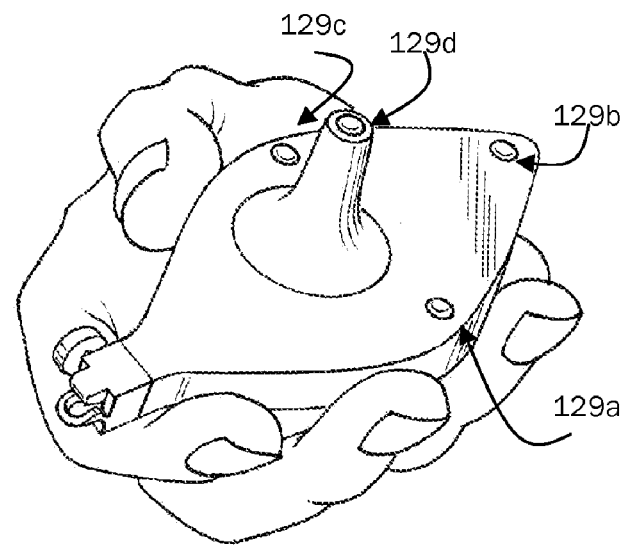
FIGS. 2A and 2B illustrate an example of a transmit antenna assembly and its associated geometry that may advantageously be used with the present invention.
Figure 2B:
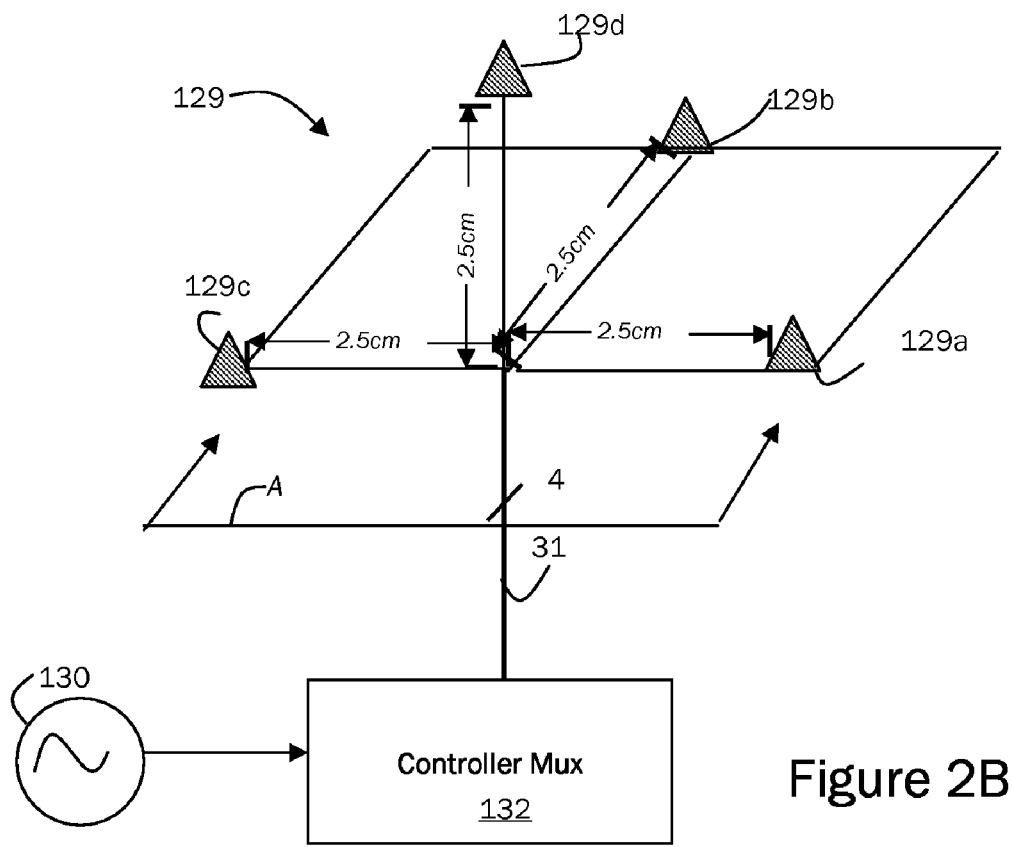

In FIG. 2A an example of a transmit antenna assembly 129 (FIG. 2A) that may be provided on the marker 29 or instrument is shown. FIG. 2B is a diagram illustrating an exemplary geometry of the transmit assembly 129. In one embodiment, each transmit assembly comprises four antennas arranged in a pyramid, with 3 antennas disposed on plane A and the fourth raised off the plane. Each transmit assembly 129 is coupled to a controller 132, (located either in the transmit circuitry 22 or in distribution box 24) via a shielded wire lead. The leads, shown as a group 31 in FIG. 2B, are advantageously bundled but individually shielded to prevent crosstalk. As shown in FIG. 2B, the antennas are generally arranged as a triangular based pyramid, although other arrangements are possible. Each of the four antennas (129a, 129b, 129c, and 129d) is located at one apex of the pyramid. In an exemplary embodiment, each edge of the pyramid may measure 2.5 to 5 cm, which translates into 0.5 to 1.0 wavelength of a 5.9 GHz signal. Antenna assemblies may advantageously be packaged in groups of multiple assemblies (four, six or the like) to support navigated medical environments that utilize large numbers of anatomical markers and instruments. Marker assemblies may be formed from plastic or other disposable material with the antenna embedded therein, while antenna assemblies for instruments may be mounted so as to be removable for sterilization.

Referring back to FIG. 1, in some embodiments a distribution block 24 may be disposed between the transmitter circuitry and the transmit antenna assemblies 29, 26, although it is not a requirement of the invention. The distribution block includes an internal switch for switching the delivery of signal 27 to the antenna assemblies 26 and 29 via leads 27a and 27b to sequence the transmission of the signal 27 among transmitter antennas in the navigated medical environment 10.

The signals transmitted by the transmit assemblies are received by a plurality of receiver antennas 25a-25f. The receivers may be distributed in a spaced semi-circular, circular or other arrangement above or around the patient. Together the receivers provide a frame of reference for determining a relative position of each instrument and marker. One method of calibrating receiver position to provide the frame of reference will be described in more detail below.

The receive antennas 25a-25f forward the received signals to receiver circuitry 20. In one embodiment a distance between a receiver antenna and a transmit antenna is determined in response to a measured phase difference between a reference signal 21 received from the transmit circuitry 22 and the signals received by receive antennae 25a-25f.

Figure 3:
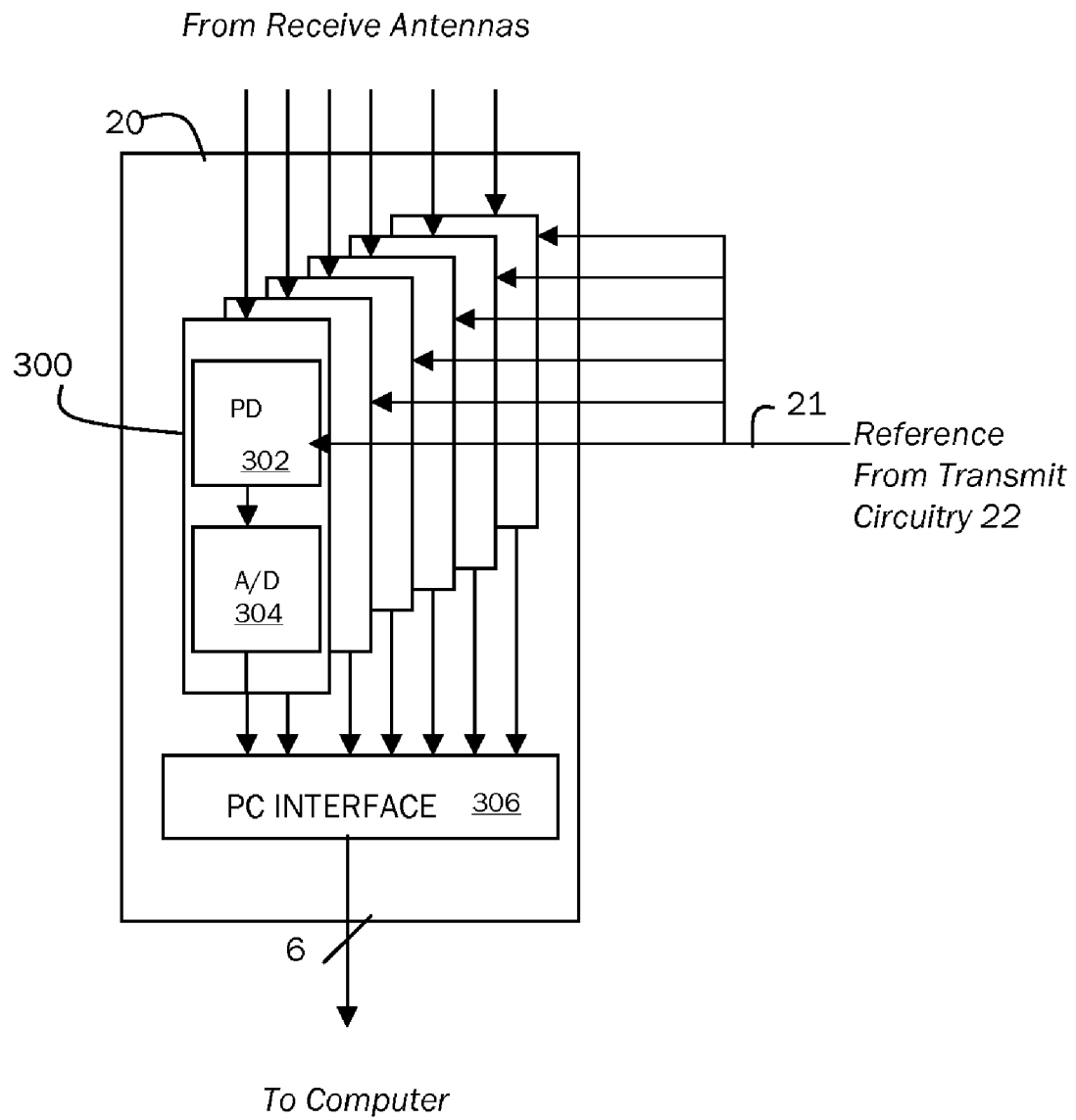
FIG. 3 is a block diagram illustrating exemplary components of a receiver of the present invention.

Referring briefly to FIG. 3, several components that may be included in an exemplary embodiment of receive circuitry 20 are shown. A receiver 300 is associated with each receive antenna. Each receiver 300 includes at least one Phase Discriminator (PD) 302 and at least one analog to digital converter (A/D) 304. Each receiver is coupled to receive at least one reference signal 21 from the transmit circuitry 22. As will be described in more detail below, in one embodiment each receive antenna may receive a signal transmitted at multiple wavelengths to assist in resolution of absolute three dimensional position; in such an embodiment the receiver would include filters, PDs and A/Ds for each wavelength. (Such an embodiment is described in more detail in FIGS. 17 and 18.) The A/D 304 of each receiver 300 provides a digitized representation of the phase difference between the reference signal and the associated received signal to the computer 14 via an interface 306. The digitized phase difference from a particular receiver is used to derive a distance between a transmitting antenna and the receiving antenna coupled to that receiver. The derived distances are processed by the computer to determine a three-dimensional position of a transmitting antenna with regard to a frame of reference. It will be appreciated that although the below embodiment describes the measurement of distance between a receiver and a transmit antenna using phase difference the present invention is not limited to any particular type of measurement. Rather, measured distances can be determined using any variety of techniques, including but not limited to phase discrimination, time difference of arrival and other means.

Referring back to FIG. 1, according to several aspects of the invention, the computer system comprises a plurality of program modules that are advantageously used to increase the precision of a three dimensional position determination in a navigated medical environment. A Receiver Calibration (RC) module 16 comprises program code for controlling the transmission of signals via antennas and the analysis of distances derived from signals received by antennas to calibrate positions of receive antennas for initialization of the system 12. A Line of Sight (LOS) program module 17 gathers and analyzes historical signal components and derived distance data for each receiver to determine a confidence weight to associate with the receiver's derived distance, thereby alleviating the impact of receiver anomalies. A Multipath program code module 18 varies the frequency of the signal 27 to provide a signal having a repeating pattern of unique frequencies to minimize the effects of multipath interference. An Absolute Position (AP) module 19 controls the transmission of multiple high frequency signals with strict phase coherence to increase precision of three dimensional position calculations. As will be apparent from the below description, each of the modules may be used independently in any navigated medical environment to improve the precision of position determinations. Each will now be described in more detail below.

Tolerance of Obstructions in the Line of Sight

In many applications, it is important to accurately maintain the position of an object, even when the line of sight between an antenna coupled to the object and one or more of antennas in the frame of reference is obstructed. Such obstructions occur routinely during the normal movement of medical personnel during navigated procedures. When a receiver is obstructed, the signal that travels the straight path may be attenuated and the phase angle measurements for that transmit antenna-receiver pair can be compromised.

Mathematically, the tracking of an object in three dimensions using RF or microwave signals requires at least one antenna on or embedded in the object and at least three other antennas at precisely known locations in the frame of reference. The signals between the antenna on the object and each of the three other antennas are converted to raw distances between the respective antennas. These raw distances are measures of the linear physical distance in three-dimensional space (that is, in the frame of reference) between the phase centers of the respective transmitting and receiving antennas. For example, signals may be transmitted from the object to the other antennas, where they are forwarded to receivers for analysis and conversion into raw distances. Measurements obtained from one transmitting antenna to additional receiving antennas should theoretically resolve to the same point. However, if the signal between a receiver-transmit antenna pair is temporarily compromised, a measurement for that pair may resolve to a different point.

According to one aspect of the invention, accurate three dimensional tracking of an object is provided even when line of sight is obstructed by calculating raw distances between the object and some number of receiving antennas greater than three and associating confidence measurements to the respective raw distance measurements. During a successive approximation process, the confidence measurement is applied to a difference calculation between the raw distance and a derived distance associated with an estimated position of the object. The confidence weight thus controls the impact that a particular raw distance calculation has on the overall estimated position calculation.

The confidence weight can be used to reduce the impact of a measurement with intermittent anomalies (either in the raw distance itself or in components that are used to derive the raw distance measurement) or a measurement that is historically trending in an unexpected, divergent manner. In existing technology, when signals between the object and the sensors in the frame of reference become compromised, the navigated surgery system is disabled, alarms are sounded, and the delivery of care to the patient is suspended until those signals and the tracking of the object can be restored. Such discontinuity is both frustrating and dangerous.

In the present invention, multiple redundant antennas at precisely known locations in the frame of reference are used, and confidence weights are applied to raw distances in order to mitigate the impact of factors that might compromise the signal from the object, including factors such as obstructions in the line of sight between a transmitting and receiving antenna. Moreover, since confidence weights are updated for every signal transmitted between the antenna on the object and every receiving antenna, it is a self-correcting influence on position calculations without resulting discontinuity in service. Various embodiments of this invention will include four or more receivers to improve reliability and accuracy; even if one or more receivers becomes partially or totally obstructed for a period of time, the remaining receivers can be used for position determination without the need to discontinue use of the system.

Figure 4:
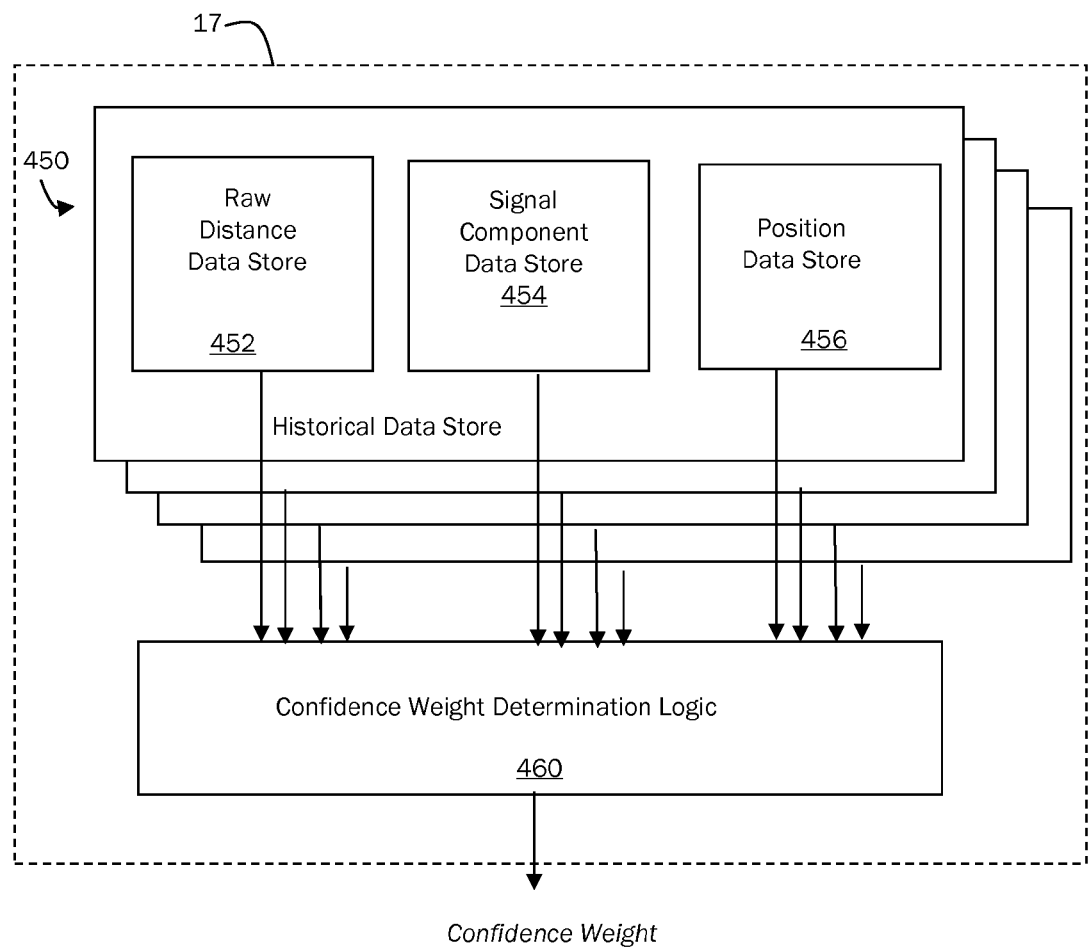
FIG. 4 illustrates exemplary components of a historical data store that may be used to generate a confidence weight for a respective transmit antenna/receive antenna pair.

FIG. 4 illustrates a historical data store 450 that may be used by LOS module 17 to determine a confidence weight to associate with each transmit antenna/receiver pair. As will be described in more detail below, each transmit antenna may also transmit multiple frequencies, and there may be a set of the data stores 450 for each frequency of the transmit antenna/receiver pair.

The data store 450 includes a plurality of data stores including a raw distance data store 452, a signal component data store 454 and a position data store 456. The data stores store may be arranged as first-in first-out (FIFO) buffers that store information used in M previous position determinations. In one embodiment, M may be, for example, five or six, but it will be recognized that the selection of a FIFO depth is a matter design choice. The raw distance data store 452 stores the raw distance results for the transmit antenna/receiver pair. The signal component data store 454 stores various signal measurements performed by the receiver for the transmitted signal, including but not limited to signal strength and phase angle. The position store 456 stores the previously generated position of the object. It should be noted that although various data stores are shown by way of example, the present invention is not limited to the use of any particular combination of historical values when generating the confidence weight but rather it is envisioned that any data associated with a received signal may be used to derive a confidence weight for a transmit antenna/receiver pair.

The confidence weight is determined by the confidence weight determination logic using any combination of data in the historical data store. The confidence weight can be determined using both information related to one transmit antenna/receiver pair, and also through the comparison of the information with other transmit antenna/receiver pairs. In one embodiment, a confidence weight may be generated through an analysis of a subset of historical data to determine the standard deviation of the subset. In some embodiments the standard deviations may be averaged, while in other embodiments the highest standard deviation may be used. A confidence weight may be assigned to the raw distance measurement that is the inverse of the standard deviation of the subset. Thus if a particular result or component is noisy, the resulting confidence weight will reduce the impact that such a result has in the determination of position. Other methods of evaluating the data and determining a confidence weight using statistical methods or other techniques are considered equivalent hereto and the present invention is not limited to any particular method of parsing the historical data to determine a confidence weight.

Evaluating the historical data in this manner helps to identify a trend in receiver operation, or a divergence of a receiver from its trending behavior both at a signal component, distance measurement and position determination granularity. Among the trends that can be discovered are the rate of change of distance between successive measurements, deviation in distance as measured by signals of different frequencies, and relative noisiness of successive measurements. For example, if a particular receiver detects rapid variations in the phase angle, suggesting that the object is moving, while other receivers detect no change, then the confidence measure of the particular receiver should be lowered. Also, if an intensity of a signal between a transmit antenna/receiver pair is substantially weaker than other pairs and/or substantially weaker than historical values of the pair, the confidence weight is lowered.

In one embodiment, the position estimate may store both a historical position of the object as well as a position determination made without incorporating the information from the particular transmit antenna/receiver pair. If the two positions diverge, then the confidence weight associated with the transmit antenna/receiver pair is lowered.

When calculating the three dimensional positions of objects, these measures of confidence are applied as weighting factors for each receiver-transmit antenna pair. If a pair has full confidence, then its distance will be used with full weight to calculate location. Pairs with lower confidence will have proportionally less impact on the location calculation. The more receivers, the more data will be provided, thereby improving the accuracy and reliability of the system.

Figure 5:
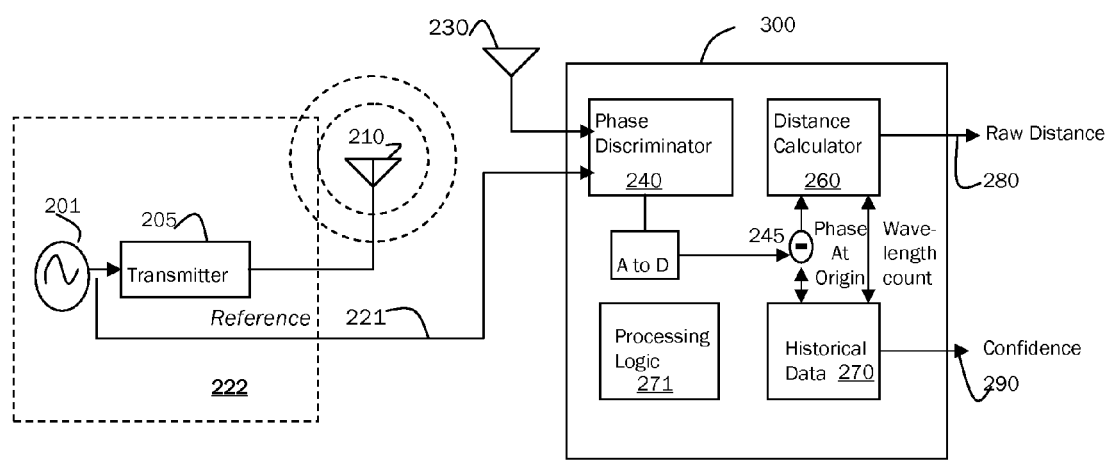
FIG. 5 illustrates components that may be included as part of receiver logic for generating a confidence weight.

FIG. 5 illustrates additional components that may be included in a receive circuit 300. A transmit circuit 222 provides an input RF or microwave signal 201 of the desired frequency to transmitter 205, which in turn transmits that signal via transmit antenna 210. (Transmit antenna 210 corresponds to any of transmit antennas 26a-26d in FIG. 1.) The signal 201 is also forwarded as a reference signal 221 to receiver 300. Receiver 300 is coupled to a receive antenna 230 (which corresponds to any of antennas 25a-25f of FIG. 1) and includes a phase discriminator 240, a recorded phase reference at the origin 250, a distance calculator 260, an historical data store 270, and processing logic 271. The outputs of receiver 300 are a raw distance 280 and a confidence weight 290. Input signal 201 is transmitted at periodic intervals by transmitter 205 and antenna 210 to receiving antenna 230. The output of receiving antenna 230 is amplified and sent to phase discriminator 240.

Phase discriminator 240 determines the phase angle between the received signal and reference signal 221. The result is digitized and subtracted from the stored phase reference at origin 250 to provide a phase change. This phase change represents the difference between the phase of the signal received by this particular receive antenna 230 from this particular transmit antenna 210 with the object at its present location and the phase reference determined for this particular transmit/receive pair at the origin. The digitized result is applied to geometric distance calculator 260, which converts phase change into distance and uses historical data 270 to add the appropriate number of whole wavelengths. This sum is the raw distance 280 between the transmit and receive antenna, in particular, between their phase centers. It will be appreciated that a distance, if calculated from the current phase angle alone could only determined modulo the wavelength of the transmitted frequency. Therefore, in a practical implementation, distance calculator 260 retains the raw distance from the previous interval and calculates the raw distance 280 of the present interval to be within one wavelength of the previous distance.

It will be appreciated that there are many ways to calculate the raw distance between the origin and the moving antenna. For example, instead of subtracting the phase angle from the phase reference at the origin, a calculation may differentiate and then integrate the phase angle. All such ways are within the scope of this invention.

The output of the digitized data from phase discriminator 240 is also applied to historical data store 270, which retains the phase information and other information from the previous position determinations, including the data records illustrated in FIG. 4. The historical data is used to calculate confidence weight 290 using the techniques described above.

Figure 6:
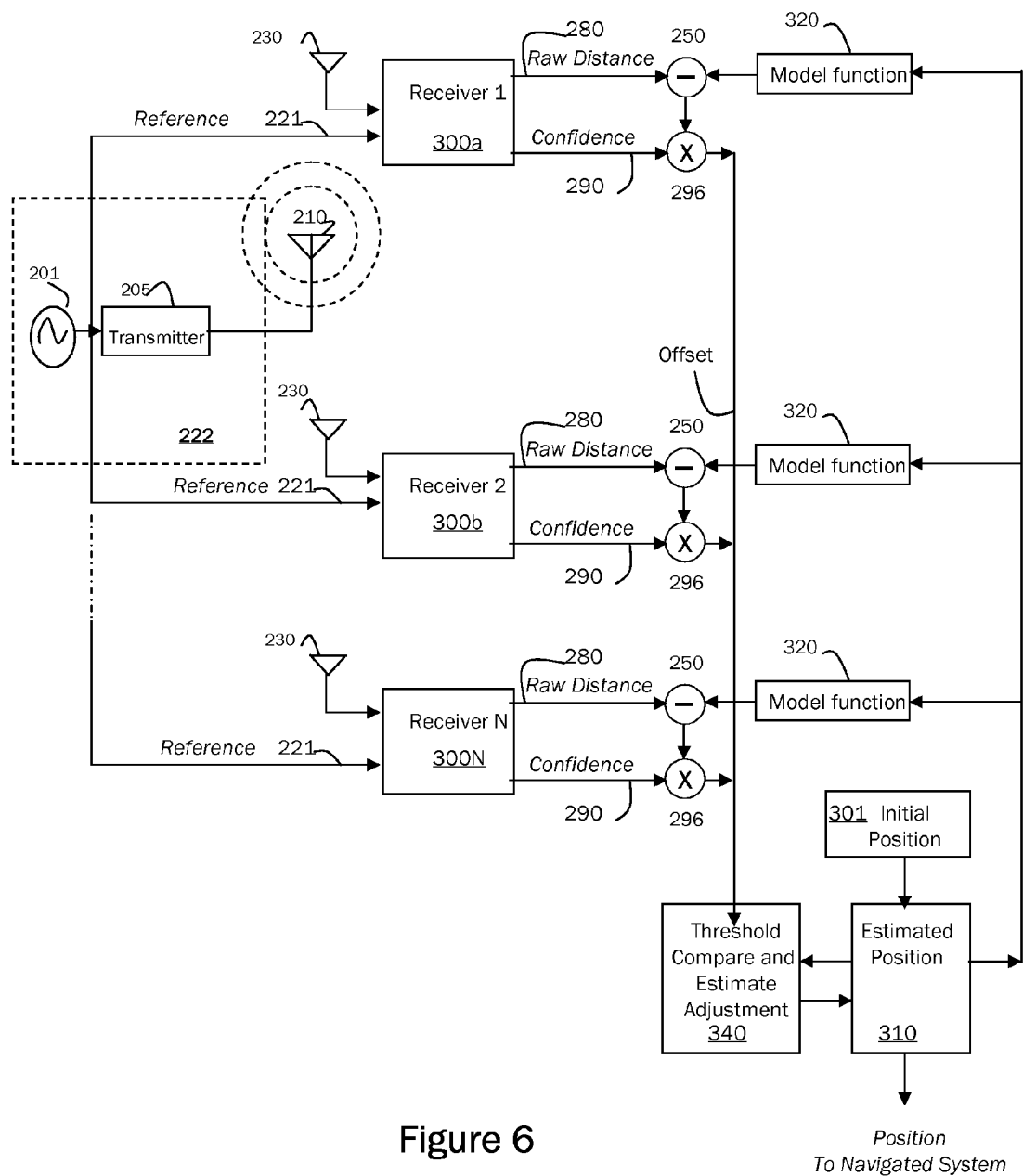
FIG. 6 is a block diagram of a navigated medical system that incorporates a confidence weight into a position calculation process such as that of FIG. 7.
Figure 7:
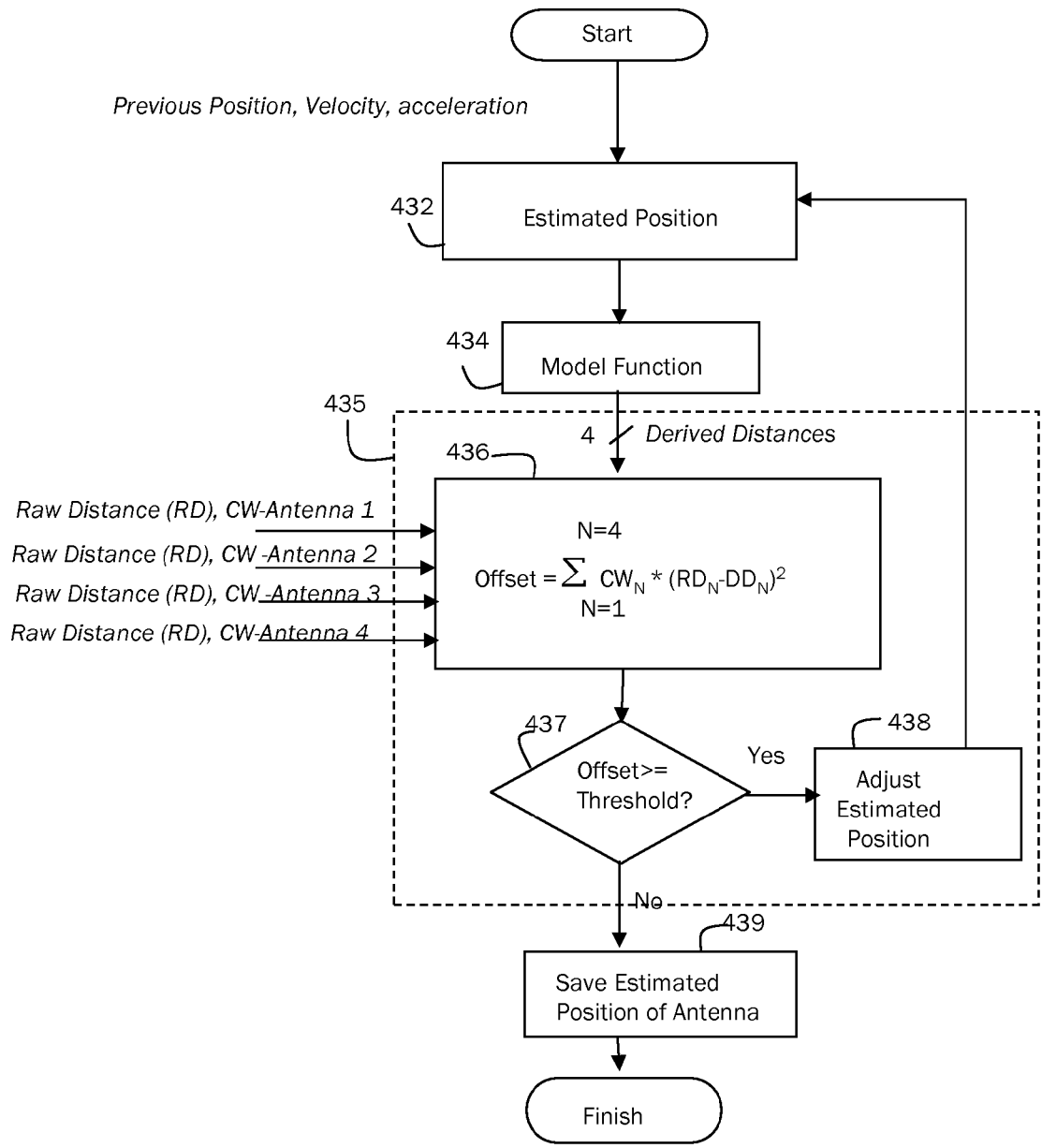
FIG. 7 is a flow diagram illustrating exemplary steps that are performed in a minimization process used to determine a position in the system of FIG. 1.

FIG. 6 is a diagram of a multi-receiver navigated medical environment which will be used to describe how the confidence weights may be applied to determine absolute position of the object by a method of successive approximation. FIG. 7 is a flowchart illustrating the successive approximation method. With regard to FIG. 6, at periodic intervals, each receiver (300a-300n) receives a signal from each transmit antenna 210 (i.e., 26a-26d of FIG. 1). The receiver than determines a raw distance and confidence weight corresponding to each transmit/receive antenna pair (and potentially, as will be described below, for different frequencies of the transmit antenna/receiver pair). The raw distances are compared by comparators 250 against estimated distances 321 derived from estimated position 310 via model functions 320. The results of the comparison are multiplied by the confidence weight of the receivers at multipliers 296, and the results are combined into an offset that is forwarded to a Threshold Compare and Estimate Adjustment module 340, which adjusts the estimated position and forwards it to module 310. As described in FIG. 7, the estimated position is repeatedly adjusted until the offset is within a desired threshold, at which point the estimated position is deemed to be the actual position of the object and can be forwarded to the Navigated Surgery workstation 12 (FIG. 1).

FIG. 7 depicts a functional flow diagram of the method of successive approximation in a preferred embodiment. An initial estimated position 432 (corresponding to 310 in FIG. 6) is determined. A Raw Distance ($RD_N$) and advantageously a confidence weight ($CW_N$) are determined for each transmit/receive antenna pair and are forwarded to the comparison block 435 of FIG. 7 (corresponding to 340 of FIG. 6). The loop of FIG. 7 is an iterative process that determines the quality of the estimated position of the object with respect to distances derived from that estimated position and updates the estimated position to improve that quality.

In one embodiment, information regarding a previous position may be used to provide an initial value of the estimated position variable 432, although it is not a requirement. The estimated position is forwarded to a model function 434 (corresponding to 320 in FIG. 6) that derives distances $DD_N$ between each transmit/receive antenna pair using a mathematical formula. The derived distances are forwarded to a minimization process 435.

Raw distance and confidence weights associated with each transmit/receive antenna pair are also forwarded to the minimization process 435. In a preferred embodiment, process 435 uses a standard Levenberg-Marquardt technique to speed the convergence of a series of successive estimated positions of the object within a reasonable number of iterations to the actual position of the object.

Thus at step 436 an offset between derived and raw distances is calculated using Equation 2 as follows:

$$\text{offset} = \sum_{N=1}^{N=TA_{Num}} CW_N * (RD_N - DD_N)^2 \quad \text{(eq 2)}$$

where $CW_N$, $RD_N$ and $DD_N$ are respectively the confidence weight, raw distance and derived distances associated with the relationship between the Nth transmit-receive antenna pair, and $TA_{NUM}$ is the total number of such receive-transmit antenna pairs. The offset is thus the sum of the squares of the weighted differences between the derived and raw distances.

The offset serves as a numerical indication of the quality of the estimated position. If the offset is near zero, then either all of the raw distances are very close to the derived (measured) distances, or the few raw distances that are far from their corresponding derived distances are weighted so low as to have little impact on the position. Thus, a small offset value implies that estimated position of the object is very near the actual position. If the offset is much larger than zero, the estimated position of the object is correspondingly farther from the actual position. At step 437 the offset is compared against a predetermined threshold based on the required precision of the position of the moving object. If the offset is within the threshold, the position determination is complete, and the calibrated receiver position is stored at step 439. If the offset is not within the threshold, then at step 438 the estimated position is adjusted and the process returns to step 432, where the minimization process 435 is repeated with the new estimated positions until the offset is within the desired threshold.

It is appreciated that one method of adjusting the estimated position is to use Jacobian adjustment techniques to expedite determination of an estimated position, although other methods, such as random and incremental adjustment may be used and the present invention is not limited to the use of any particular manner of adjustment. In one embodiment, to improve the accuracy of calibrating each of the receiving antennas, a plurality of input RF or microwave frequencies may advantageously be used. This minimizes the effect of multipath distortion and other interference.

It will be appreciated that although a particular process for calibrating an object position has been described in FIGS. 7 and 6, the present invention is not limited to the use of any particular position determination process or algorithm. The process of FIG. 7 may be repeated for each instrument in the navigated medical environment.

It will be appreciated that other embodiments within the scope of this invention may use other minimization criteria to determine the best estimate of the position of the object from imperfectly received signals.

Figure 8:
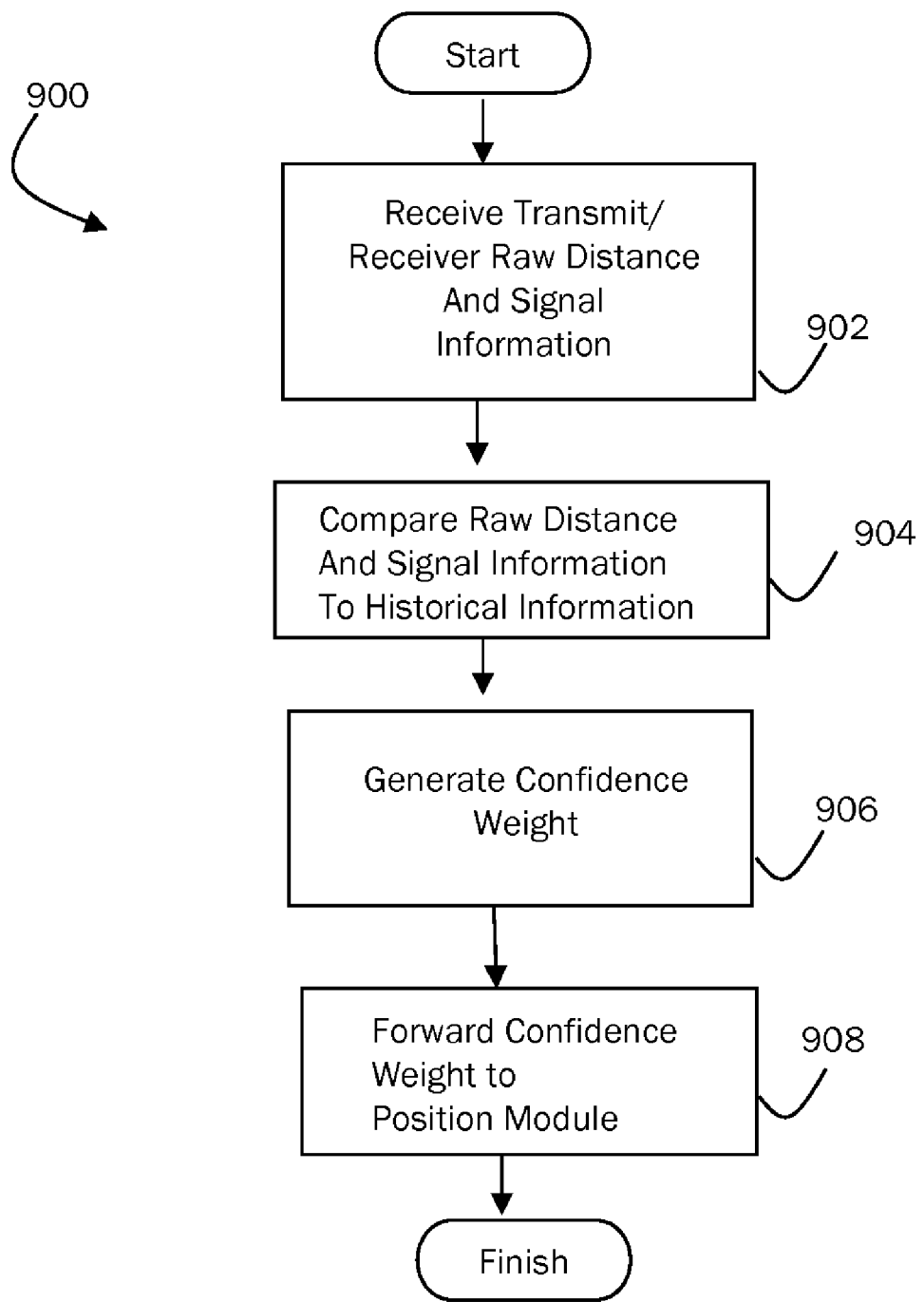
FIG. 8 is a flow diagram including exemplary steps that may be taken to generate a confidence weight.

FIG. 8 is a flow diagram illustrating exemplary steps in a process 900 that may be performed by the LOS module to determine a confidence weight. At step 902 the LOS module receives the raw distance and other signal information for each transmit/receive antenna pair. At step 902 the LOS module analyzes the received information in view of data in the historical data store and generates a confidence weight at step 906. At step 908 the LOS module forwards the confidence weight and raw distance information to a positioning module 19.

It should be understood that the confidence weight of this invention may be used to validate the reading of any device, and that the direction of transmission between a fixed and moving antenna is irrelevant. That is, the method works equally well if a) the transmitting antennas are attached to the object and the receiving antennas are part of the frame of reference, b) the receiving antennas are attached to the object and the transmitting antennas are part of the frame of reference, and c) some combination of the transmitting and receiving antennas are attached to one or more moving objects and the remaining are the part of the frame of reference.

Accordingly, a system and method for ensuring the accuracy of positional information in an environment where line of sight obstruction and other interference is present has been shown and described. Maintaining a history of receiver behavior and weighting the confidence given to the receiver measurements based on past behavior minimizes the impact of receiver anomalies, blockages in the line of sight between a transmitting antenna and a receiving one, poor signal strength, or other factors. Providing a multiplicity of receivers and using confidence weights to control the use of the received data in position determinations increases the reliability and accuracy in a navigated medical environment by allowing self-correction to reduce disruptions to service.

Antenna Calibration

In order to accurately track the positions of objects using phase differences or time differences of arrival of RF or microwave signals, it is crucial that the precise locations of the antennas in the frame of reference be known to the desired degree of precision. It is also crucial that the precise locations of the antennas on each movable object be known with respect to an internal coordinate system of that object, also to the desired degree of precision. For example, in navigated medical procedures this precision is in the range of 0.5 mm, and therefore, it is necessary to know the location of each antenna with a precision of at least 0.25 mm, so that the distance between them can be known to the nearest 0.5 mm.

However it is often difficult to determine any antenna position to this degree of precision. For example, in an application of tracking surgical instruments, the receiving antenna array may be up to 2 meters in diameter and may be mounted on a movable cart. It is highly impractical for a surgical technician to measure or control the physical placement of the cart to a precision of 0.5 mm or better. Moreover, it is necessary to know the location of not just any point on an antenna but rather its phase center. In one embodiment, the antennas on a moving object are implemented as printed circuit elements approximately 12 mm long and 6 mm wide. Locating the phase center of such an antenna to within 0.5 mm is also highly impractical. In some antennas, the phase center may vary with the frequency being transmitted, and the variance may be greater than the required precision for tracking an object. In these cases, the position of the phase center must be known as a function of signal frequency.

In the present invention, a priori knowledge of the locations of the phase centers of the antennas in the frame of reference is not required. Instead, these locations are determined by a system calibration process prior to the start of each navigated procedure. In one embodiment, the method may use a precisely manufactured calibration tool containing a plurality of transmit antennas with known geometry and known phase centers. One exemplary embodiment of such a calibration tool is the assembly of FIGS. 2A and 2B.

In another embodiment, a calibration device comprises a single antenna mounted on a precision motion control machine so that the antenna can be moved to different locations during the system calibration process. Commercially available motion control machines suitable for this purpose have precisions in the range of tenths or hundredths of a millimeter or better.

The method of determining the locations of the antennas of a frame of reference is similar to that of tracking moving objects, but with a fundamental difference—there is no "phase reference at the origin." That is, there is no a priori known phase angle with respect to which the phase of a particular signal can be compared. Therefore, it is not possible to determine precisely the raw distance between an antenna on the calibration device and an antenna in the frame of reference. Since the calculations of Equation 2 and FIG. 7 depend upon raw distances, they break down during system calibration.

Figure 9:
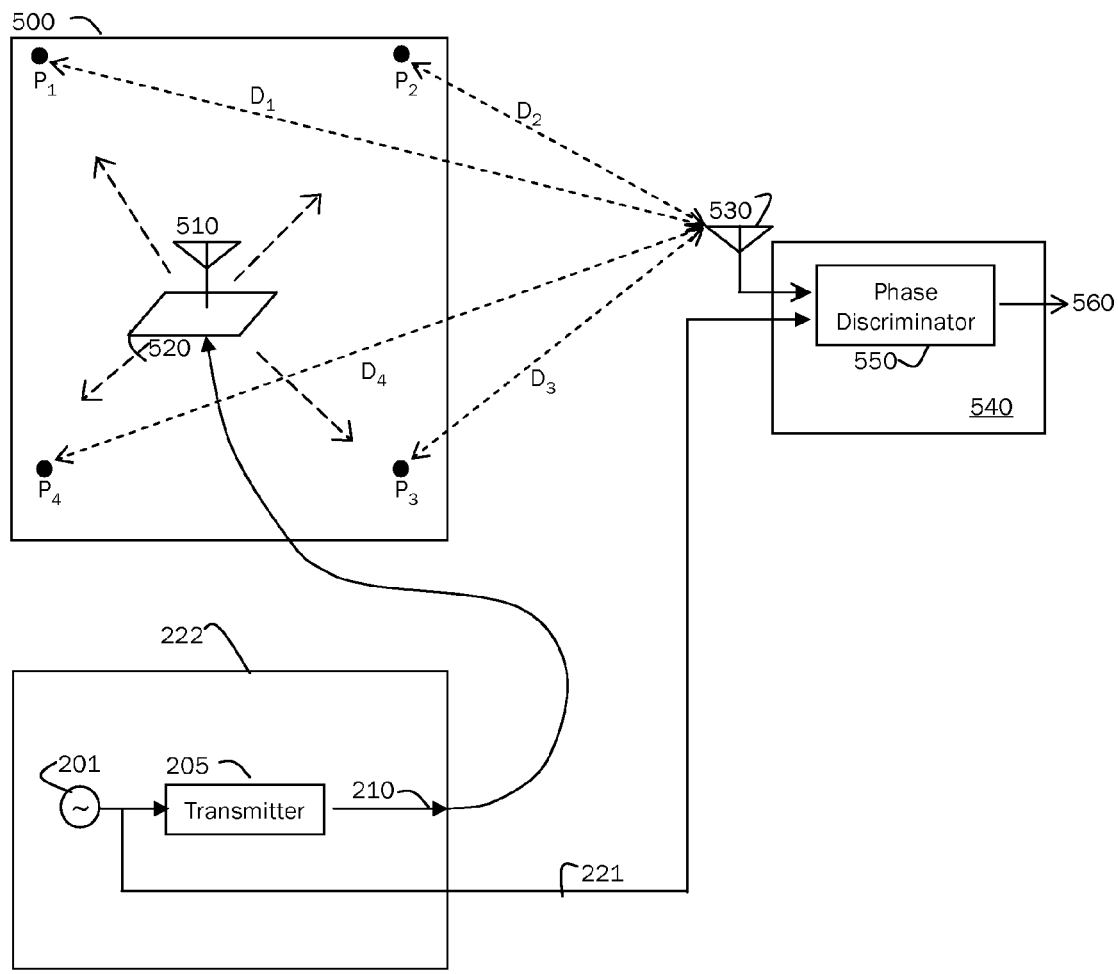
FIG. 9 is a block diagram illustrating a calibration device of the present invention including a single antenna and a precision movable platform.

Consider first a calibration device with a single antenna and a motion control machine. A diagram of an example is depicted in FIG. 9. Transmit circuitry 222 is coupled to calibration assembly 500, which contains a movable platform 520 on which is mounted transmit antenna 510. Signal generator 201 is coupled to transmitter 205, which transmits signal 210 through transmit antenna 510. The movable platform is capable of being moved to a plurality of points, all of whose locations in three-dimensional space are known to a high degree of precision. Let a signal be transmitted from each of points $P_1$, $P_2$, $P_3$, and $P_4$ in succession to receive antenna 530, which is coupled to receiver assembly 540. Also coupled to receiver circuitry 540 is reference signal 221 from transmit circuitry 222. Receiver circuitry 540 includes phase discriminator 550, which measures the phase angle between a signal received by antenna 530 and reference signal 221.

It will be appreciated that when receiver antenna 530 and calibration assembly 500 are both fixed in the frame of reference, the only change of phase detected by phase discriminator will be due to the motion of platform 520. It will also be appreciated that distances $D_1$, $D_2$, $D_3$, and $D_4$ between antenna 530 and points $P_1$, $P_2$, $P_3$, and $P_4$, respectively, will not be known within the required degree of precision.

However, their pairwise differences can be determined from the measured phase differences. Let $\phi_1$, $\phi_2$, $\phi_3$, and $\phi_4$ be the phase differences between reference signal 221 and the transmitted signal 210 from points $P_1$, $P_2$, $P_3$, and $P_4$, respectively, to receive antenna 530. Since these phase differences are known by measurement, the pairwise differences $\Delta_{12}$, $\Delta_{13}$, $\Delta_{14}$, $\Delta_{11}$, $\Delta_{23}$, $\Delta_{24}$, and $\Delta_{34}$ between the distances $D_1$, $D_2$, $D_3$, and $D_4$ can be determined from the equations $$\Delta_{12} = (D_1 - D_2) = \frac{c}{2\pi f} \times (\phi_1 - \phi_2) \qquad (eq\ 3)$$

$$\Delta_{13} = (D_1 - D_3) = \frac{c}{2\pi f} \times (\phi_1 - \phi_3) \qquad (eq\ 4)$$

$$\Delta_{14} = (D_1 - D_4) = \frac{c}{2\pi f} \times (\phi_1 - \phi_4) \qquad (eq\ 5)$$

$$\Delta_{23} = (D_2 - D_3) = \frac{c}{2\pi f} \times (\phi_2 - \phi_3) \qquad (eq\ 6)$$

$$\Delta_{24} = (D_2 - D_4) = \frac{c}{2\pi f} \times (\phi_2 - \phi_4) \qquad (eq\ 7)$$

$$\Delta_{34} = (D_3 - D_4) = \frac{c}{2\pi f} \times (\phi_3 - \phi_4) \qquad (eq\ 8)$$

where c is the speed of light in air, f is the frequency of transmission, and the constants $k_{ij}$ represents the whole number of wavelengths to add to the difference in phases between points i and j. Each constant $k_{ij}$ can be determined by inspection, by simple measurement (e.g., a tape measure), by continuous tracking in the same way raw distances are determined when tracking an object, or by the method of short and long wavelengths described below.

Figure 10:
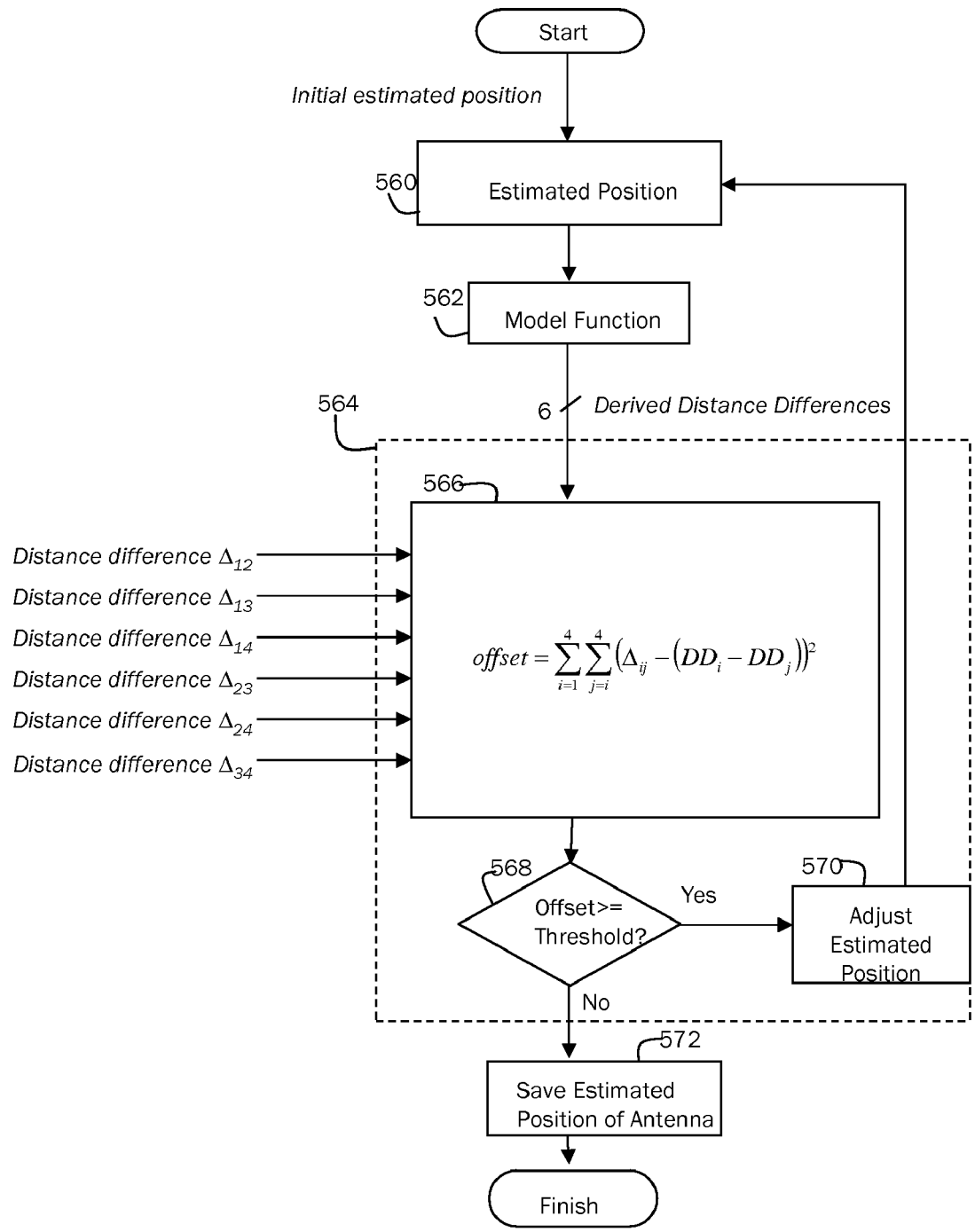
FIG. 10 is a flow diagram illustrating exemplary steps that may be performed during a minimization process to calibrate antennas in FIG. 9 or FIG. 11.

FIG. 10 is a flowchart describing a method of successive approximation to determine the position of antenna 530 relative to calibration device 500. An initial, imprecise estimate of the position is made by simple measurement, for example, by a tape measure. This is applied to estimated position 560. A model function 562 then performs a geometric calculation to determine derived distances $DD_1$, $DD_2$, $DD_3$, and $DD_4$ between the phase center of receive antenna 530 at its estimated position and the phase center of transmit antenna 510 actual position when motion platform 520 is at points $P_1$, $P_2$, $P_3$, and $P_4$, respectively. In order for the model function to determine the derived distance, it must know the exact geometry of the calibration device and the precise positions of antenna 510 at which phase angle measurements are taken.

Next, minimization unit 564 computes an offset 566 according to the following equation.

$$\text{offset} = \sum_{i=1}^{4} \sum_{j=i}^{4} (\Delta_{ij} - (DD_i - DD_j))^2 \quad \text{(eq 9)}$$

where N is the number of discrete points at which phase angle measurements are made during the calibration. In step 568, offset 566 is compared to a predetermined threshold based on the required degree of precision. If the offset is within the threshold, then the estimated position of the antenna 560 becomes the actual position of the antenna 572. Otherwise, the estimated position is adjusted in step 570, and the computation is repeated.

By this means, the phase center of the antenna 530 is determined with respect to the coordinate system of the calibration system. The method of successive approximation of FIG. 10 is repeated for each antenna requiring calibration.

Once a set of antennas has been calibrated with respect to some coordinate system, that set can be used to calibrate other antennas. For example, a precision manufactured calibration device that includes a plurality of antennas in a predetermined array could be calibrated at the factory by the methods of FIGS. 9 and 10. The positions the phase centers of its antennas would thus be known within the required precision. Moreover, any phase differences that may exist among the antennas of the set can be discovered and recorded at the same time. The knowledge of the geometry of the calibration device and the precise positions of the phase centers of its antennas is applied to the model function 562 in order to calculate derived distances $DD_i$ from the estimated position of an antenna being calibrated. The knowledge of phase differences of the antennas, if any, is applied Equations 3-8 to correct the measured phase differences.

Figure 11:
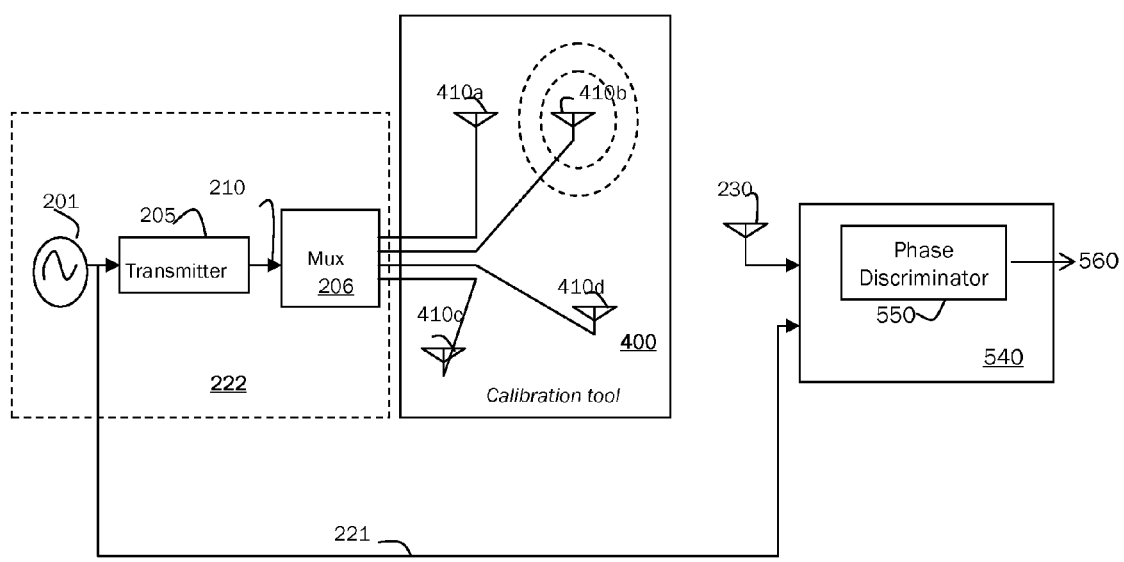
FIG. 11 is a diagram illustrating components of a calibration tool of the present invention including multiple antennas with precisely known locations.

FIG. 11 depicts a precision calibration tool 400 that can be used to carry out the system calibration of the antennas in the frame of reference prior to a navigated medical procedure. During calibration process, a signal 210 is transmitted through multiplexer 206 through each of transmit antennas 410a-410d in turn to antenna 230. Phase angles $\phi_1$, $\phi_2$, $\phi_3$, and $\phi_4$ representing the difference of the received signal and reference signal 221 are recorded. Equations 3-8 are then applied to obtain the differences in distances from the respective calibration antennas 410a-410d to antenna 230. The method of successive approximation of FIG. 10 is applied to determine the position of antenna 230 with respect to the calibration device to the required precision. The same steps are repeated for each antenna in the frame of reference. Finally, the coordinate system of calibration device 400 becomes the coordinate system of the frame of reference. That is, the origin of the coordinate system of calibration system 400 becomes the origin of the frame of reference, and the x-, y-, and z-axes of the calibration system become the x-, y-, and z-axes of the frame of reference. The calibration device can then be removed or set aside.

In a similar manner, the antennas of any object or instrument can be calibrated at the time of manufacture by the same method, but with respect to the internal coordinate system of the object or instrument. It will also be appreciated that although Equation 9 specifies a minimization of the sum of squares, a minimization of some other function of the D and the derived distances is also within the scope of this invention.

It will be appreciated that one precision calibration device with a movable platform can be used to calibrate a family of other calibration devices and instruments, and that these can be used to calibrate other devices and sets of antennas, and so on. It will also be appreciated that the same calibrations can be carried out, using the same equations, when the receive antenna is mounted on the calibration device and the transmit antennas are the ones to be calibrated.

It will be appreciated that although a particular process for calibrating receive antenna position has been described in FIGS. 9-11, the present invention is not limited to the use of any particular position determination process. Rather it should be appreciated that the concept of using a calibrated tool having fixed geometry and phase center to determine distances to an antenna can be used in a variety of navigated medical environments.

The process of FIG. 10 may be repeated for each receive antenna in the navigated medical environment. The calibrated positions of the receivers together form a frame of reference from which subsequent position determinations may be made for tracked objects in the navigated medical environment.

Accordingly, a system and method for determining a precise location of a receiver assembly for calibrating a navigated surgery system has been shown and described. Periodic transmissions from multiple antennae on a calibrated tool are received by a receiver assembly, and raw distances to the transmitting tool are calculated. A minimization algorithm is applied to determine precise location of the receivers.

Multipath

As discussed briefly above, a multipath component 18 in the computer facilitates precise distance measurement in the presence of multipath interference by sequential adjustment of the frequency of the transmitted signal 27 and appropriate filtering of received signals.

In wireless telecommunications, a multipath effect is interference in a received signal caused by the propagation of a transmitted signal along multiple paths to its destination. Reflections and refractions of the transmitted signal as it encounters obstacles before it reaches the receiver causes the transmitted signal to reach the destination via multiple paths. Each path taken by a transmitted signal will have a different length and therefore a different arrival time or phase at the receiver. Each specific frequency of a radio or microwave signal broadcast in a confined space will have a unique three dimensional pattern of positive and negative interference between the different paths. This interference pattern is referred to as a multipath effect.

Figure 12:
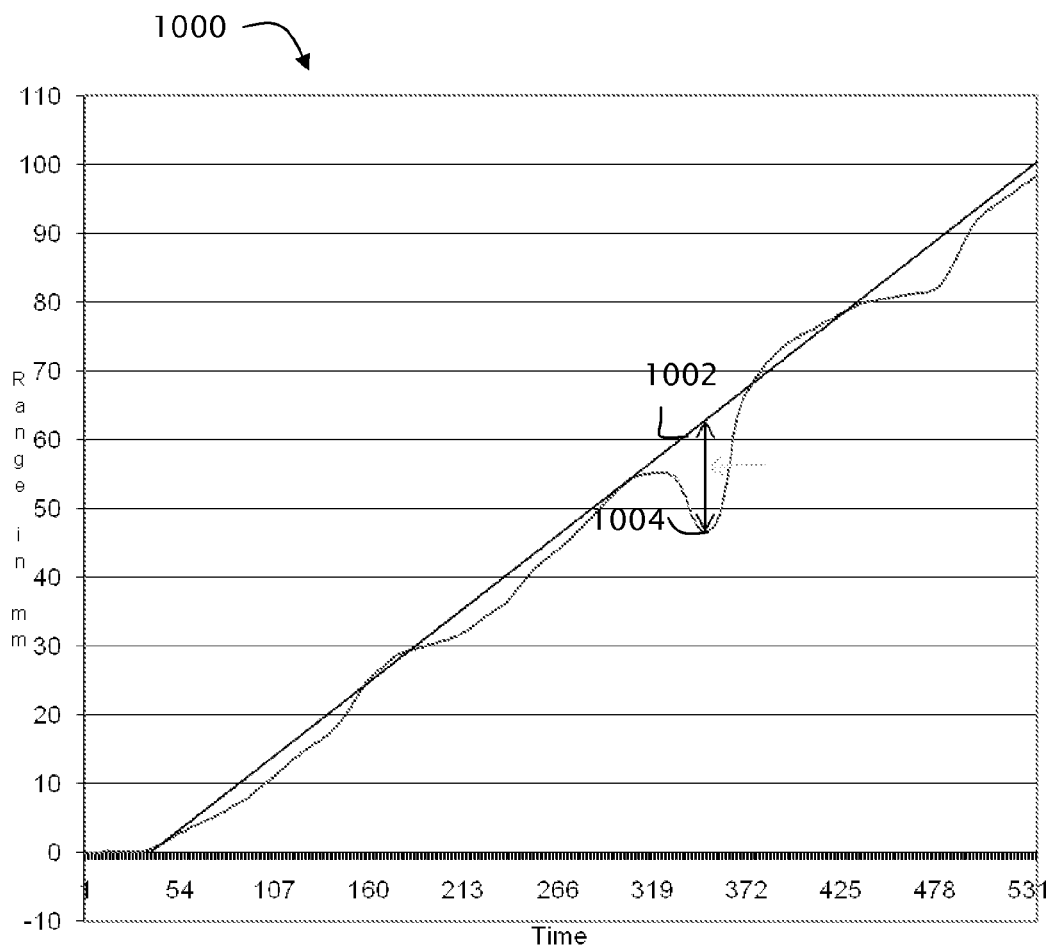
FIG. 12 is a graph illustrating the effects of multipath interference on a distance calculation.

In a navigated surgery environment, distances may be discerned by comparing the phase of a received signal against a phase of a reference signal as described above. However, multipath interference can degrade the received signal and result in inaccurate phase detection and concomitantly reduce the precision with which the position of a navigated instrument can be discerned. For example, FIG. 12 is a graph 1000 frame of reference from which subsequent position determinations may be made for tracked objects in the navigated medical environment.

Accordingly, a system and method for determining a precise location of a receiver assembly for calibrating a navigated surgery system has been shown and described. Periodic transmissions from multiple antennae on a calibrated tool are received by a receiver assembly, and raw distances to the transmitting tool are calculated. A minimization algorithm is applied to determine precise location of the receivers.

Multipath

As discussed briefly above, a multipath component 18 in the computer facilitates precise distance measurement in the presence of multipath interference by sequential adjustment of the frequency of the transmitted signal 27 and appropriate filtering of received signals.

In wireless telecommunications, a multipath effect is interference in a received signal caused by the propagation of a transmitted signal along multiple paths to its destination. Reflections and refractions of the transmitted signal as it encounters obstacles before it reaches the receiver causes the transmitted signal to reach the destination via multiple paths. Each path taken by a transmitted signal will have a different length and therefore a different arrival time or phase at the receiver. Each specific frequency of a radio or microwave signal broadcast in a confined space will have a unique three dimensional pattern of positive and negative interference between the different paths. This interference pattern is referred to as a multipath effect.

In a navigated surgery environment, distances may be discerned by comparing the phase of a received signal against a phase of a reference signal as described above. However, multipath interference can degrade the received signal and result in inaccurate phase detection and concomitantly reduce the precision with which the position of a navigated instrument can be discerned. For example, FIG. 12 is a graph 1000 illustrating the movement of a transmit antenna over time at constant velocity. The Y axis represents a range, in mm, of the transmit antenna from a receiver while the X axis is a time interval. Line 1002 represents the actual position of the transmit antenna over time, while line 1004 illustrates an apparent measured position using a received signal having multipath effects. It can be seen that the error between the apparent measured position and the actual position varies over time with the position of the transmit antenna.

According to one aspect of the invention it is realized that a distance measurement of increased accuracy can be obtained by reducing the effect of multipath interference through sequential adjustment of the transmit frequency of the transmitted signal. In one embodiment, a signal is transmitted as a repeating sequence of unique frequencies from each transmitter, with each frequency of the sequence differing by a small amount so that the wavelengths of the transmitted signals differ by small fractions. This is well known in the electronic art as frequency hopping spread spectrum. A distance calculation is then done at a receiver for each frequency, and the calculated distances are then filtered to derive a "best" distance from the object to that receiver. The sequence of frequencies is retransmitted at rapid intervals so that the object can be tracked as it moves through three-dimensional space. Switching frequencies at frequent intervals in this manner increases the accuracy of distance calculations by limiting the impact of multipath interference for each frequency.

Figure 13:
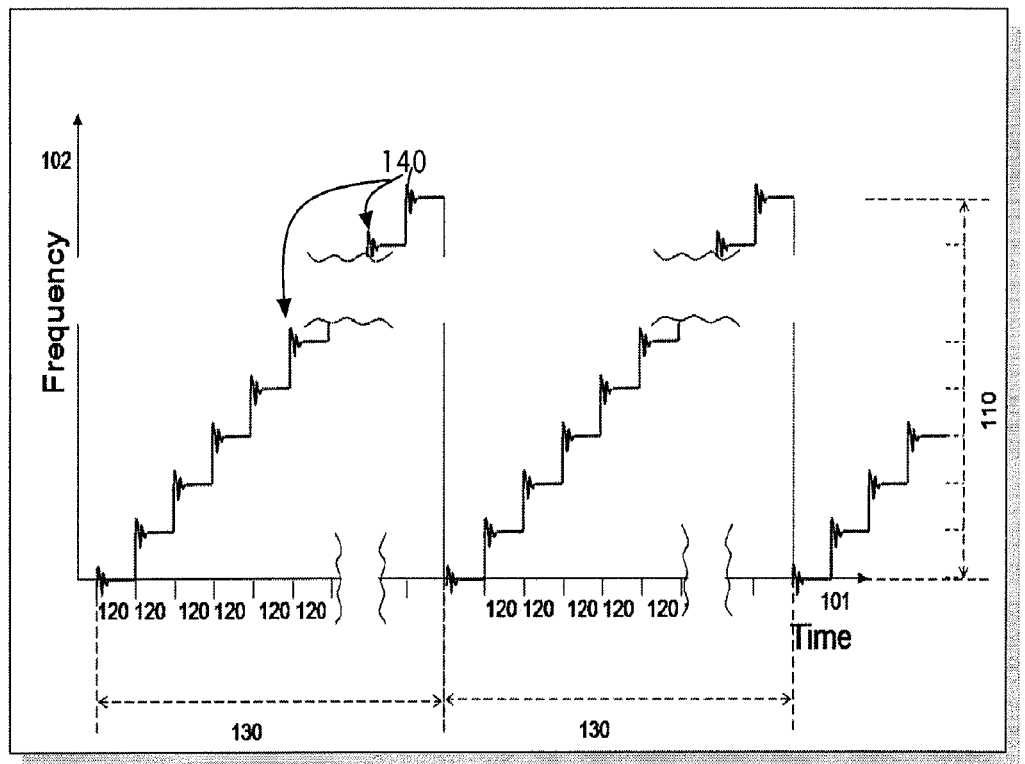
FIG. 13 is a graph illustrating one embodiment of varying frequencies of a transmitting signal by incrementally increasing the frequency of the transmitted signal.

FIG. 13 illustrates a plurality of sequences of frequencies transmitted by one transmitter over a period of time. The horizontal axis 101 denotes time, and the vertical axis 102 denotes frequency. A sequence of unique frequencies is transmitted during a sequential time interval 130. Frequency intervals 120 denote the length of time that each frequency is transmitted. It will be appreciated that in any practical embodiment, the length of each frequency interval 120 should be long enough for the transmitter to stabilize on that frequency so that a stable wave can be set up in the region of the apparatus. In particular, when a transmitter switches from one frequency to the next, there will be a short period of frequency instability 140 before a stable frequency is attained.

It should be noted that although an increasing step frequency sequence is shown in FIG. 13 the present invention is not limited to such a frequency pattern; rather any pattern of unique frequencies may be transmitted over the sequence and the present invention is not limited to any particular pattern of unique frequencies.

As described with regard to FIG. 1, in one embodiment transmit circuitry 22 includes a switch that sequentially transmits the signal out of each of the four antennas of the transmit antenna assembly during the frequency interval 120. Thus during an example sequential time interval 130, the signal 27 will be transmitted at 32 unique frequencies sequentially across each of the four antenna of a transmit assembly. The reference signal 21 also sequences through the same frequencies. The phase angle between a reference signal and the signal detected by one receiver is converted into a distance to that receiver using the knowledge of the distances determined from the previous few transmissions of the same frequency. When the distances are thusly determined for all of the frequencies of a sequence, they will vary because of the different effects of multipath distortion on the different frequencies. A filter is used to select the "best" estimate of the distance.

Figure 14:
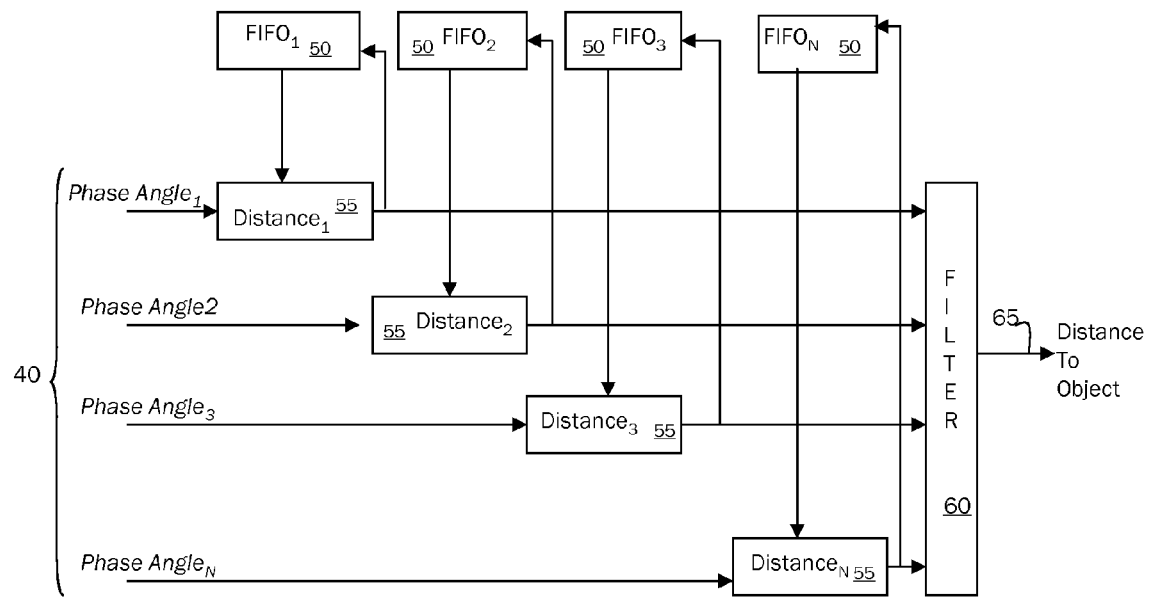
FIG. 14 is a block diagram illustrating components that may be used to estimate a distance using a plurality of phase differences associated with each of the frequency steps of the transmitted signal.

FIG. 14 shows an embodiment of circuitry which may be associated with each receiver (and located either at the receiver or as part of the Multipath component of the computer 14) to calculate a raw distance between the respective receiver and a transmit antenna using the multiple frequency phase offset information obtained as described above. For each of the N frequencies of one sequence, a phase angle difference 40 between the received signal and the reference signal for the frequency is obtained for the receiver 20 (FIG. 1). FIFO storage units 50 store a set of previously calculated distances for the frequency for the receiver from a small set of previous sequences, where one FIFO is assigned to each frequency of the sequence. Distance calculators 55 estimate the distance to the receiver based on the particular frequency, the phase angle 40, and the previously known distances in FIFO 50.

The outputs of the distance calculators 55 are coupled both to the respective FIFOs 50 and to a filter 60. The filter 60 evaluates each of the received distances and derives a distance by applying a statistical filter to the collection of derived distances. The statistical filter may be, for example, a mean or median filter. Experimentation has shown that both mean and median filters provide highly accurate estimates of the actual distance, provided that a previous reference point is established to start the process. However, it should be noted that there are a variety of other filtering methods that can be used to select a 'best' distance result. These methods include but are not limited to both statistical filtering methods (including but not limited to mean, median, standard deviation measurements and combinations thereof) as well as predictive or heuristic filtering (for example, anticipating a distance delta based on prior data) and the like.

In one embodiment of the invention a confidence weight such as that described above with regard to FIGS. 4-8 may advantageously be assigned to either each the calculated distances from distance calculator 55 or alternatively to the filtered result 65 to compensate for interference at the various frequencies.

Figure 15:
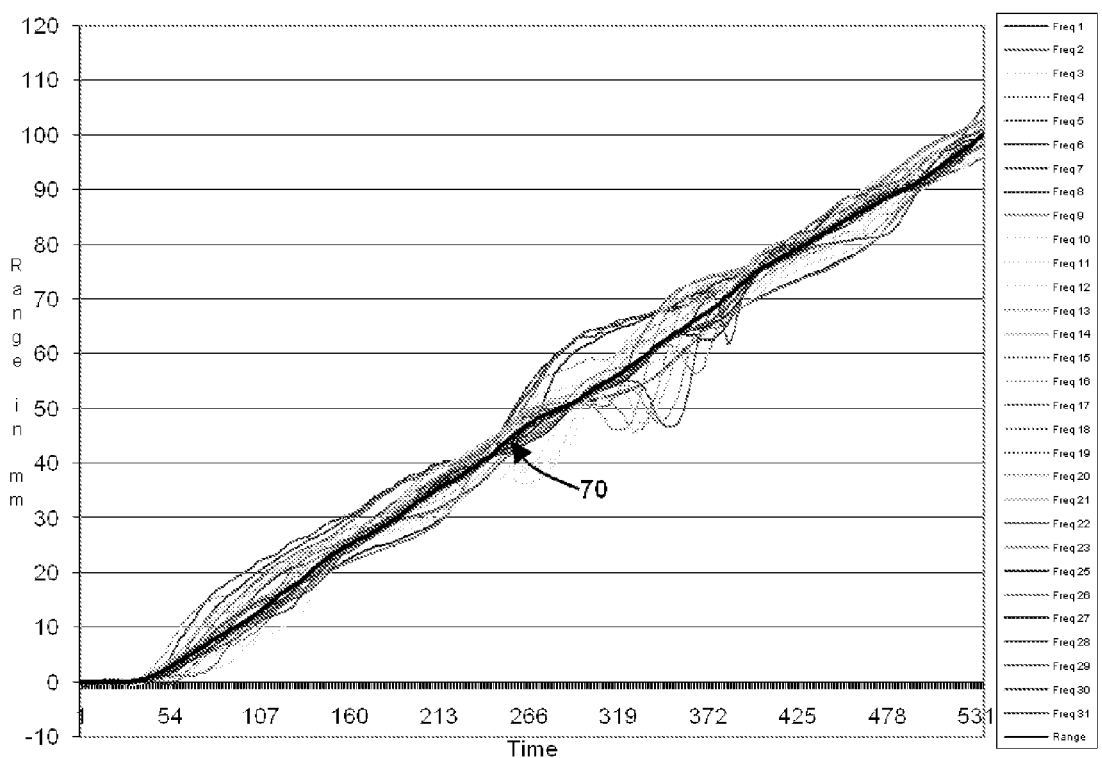
FIG. 15 is a graph illustrating a resulting estimated distance derived using the plurality of phase differences associated with each of the frequency steps of the transmitted signal.

FIG. 15 illustrates a graph of distances determined by a transmit antenna moving away from a receiving antenna at a fixed speed. Each line (other than line 70) represents the apparent distances between an object and an antenna as determined by an individual frequency. As can be seen in the plot, these frequency-determined distances fluctuate around an actual distance. Line 70 represents the distance calculated by applying the statistical filter to the derived distances obtained using the step frequencies of FIG. 13.

For example, with frequencies in the range 5.7-5.85 GHz, multipath distortion can cause the apparent distances determined for one receiver from each frequency to vary as much as several millimeters from the actual distance as measured with a precise measuring tape. However, when the distances are filtered among all of the frequencies of the sequence, the result (70) is accurate within a tolerance of less than one millimeter.

Figure 16:
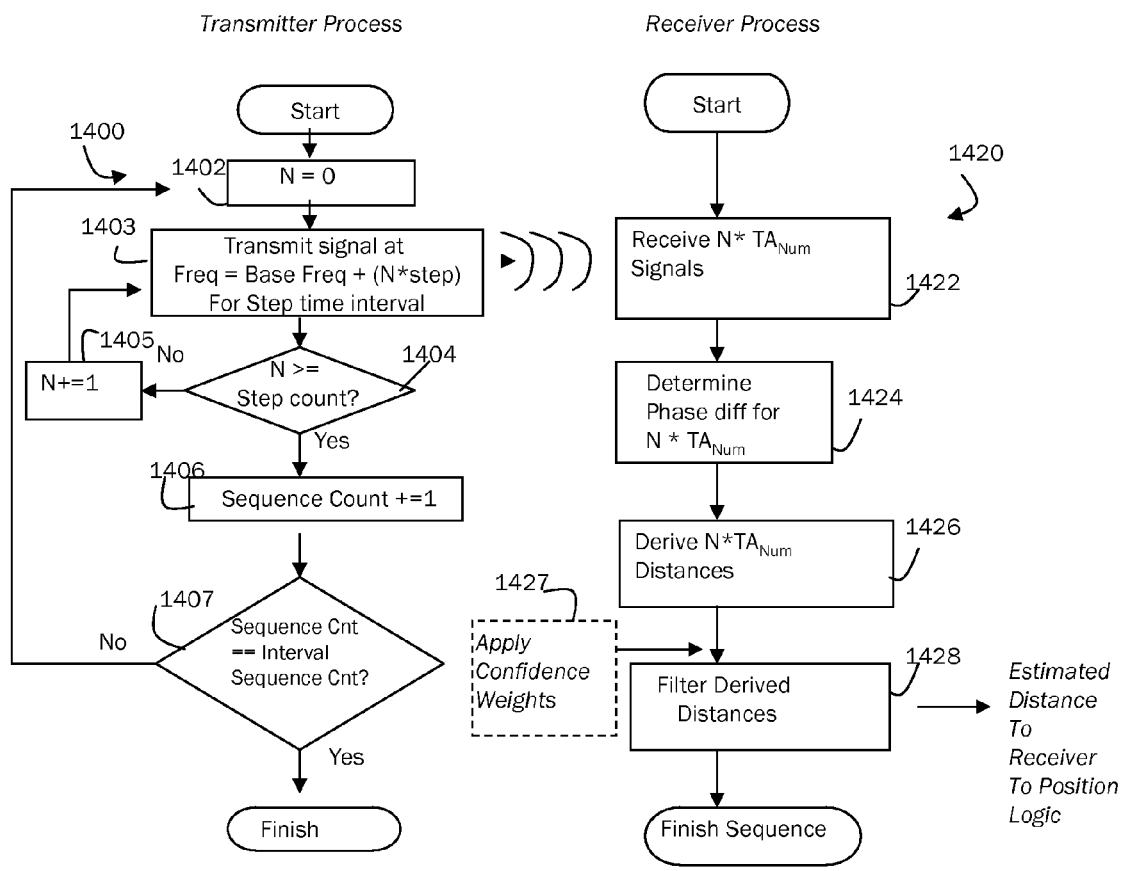
FIG. 16 illustrates flow diagrams including exemplary steps that may be performed by a transmit and receive process implementing the present invention.

FIG. 16 illustrates flow diagrams of exemplary steps that may be performed during a transmit process 1400 and receive process 1420 to minimize the impact of multi path interference according to the present invention. At step 1402 a step counting variable N is set to 0. At step 1403, a signal generator generates a signal having a frequency equal to the base frequency+the step frequency increment*N. The signal is transmitted for the step interval time. As mentioned above, the step interval time may be sufficient to allow each of a number of transmit antennas 26a-26d to transmit a stable signal to the receiver.

At step 1404 it is determined whether the number of step frequencies of a sequence has been transmitted. If not, at step 1405 the variable N is incremented by 1, and the process returns to step 1403. If at step 1404 it is determined that all frequencies in the sequence have been transmitted, then the process continues to step 1406, where a sequence count is incremented. At step 1407 it is determined whether the number of sequences per interval has been processed. If not the process returns to step 1402. If the all sequences in the interval have been transmitted, then the transmit process is complete and a position of the instrument can be determined.

While logic associated with the transmitter is executing process 1400 the receiver is executing process 1420. At step 1422 the receiver continuously receives signals from the transmitter, a total of N*TA$_{NUM}$ (where TA$_{NUM}$ is equal to the number of antennas per transmit antenna assembly). At step 1424 the receiver determines the phase difference between the received signals and associated reference signals for each of the frequencies in the sequence. At step 1426 a distance is derived for each of the frequencies in the sequence. At step 1427 a confidence weight may optionally be applied to the derived distance to reduce the impact of derived distances that display anomalies. At step 1428 the derived distances are filtered using a statistical filter to identify a 'best' distance between the receiver and transmit antenna. This distance is passed to positioning logic to identify a three dimensional position of the instrument, for example using an iterative process such as that described above with regard to FIG. 7.

It will be appreciated that other embodiments of this method can determine the distance between a transmit antenna and a receiver in the presence of multipath distortion. In particular, many embodiments implement the method in software, and some embodiments integrate the distance derivation with other calculations and the feedback of other information to the FIFOs 50.

It will also be appreciated that in a system with multiple transmit antenna assemblies, the intervals 120 from each transmit antenna assembly can be interleaved, so that multiple objects can be tracked at the same time.

In addition, although the description has described the process from the perspective of a transmit assembly associated with an object forwarding a signal to a receive antenna in a frame of reference, it is recognized that a similar method may be used to locate the position of a receive antenna for example by transmitting from a calibration tool. In addition, it is appreciated that a navigated surgery system that uses mounted transceivers to track an object that includes only a receiving antenna may advantageously benefit from application of the multipath interference reduction methods of the present invention. Such an embodiment will be described later herein.

Accordingly a method and system for precisely determining a distance between a wireless transmit antenna and receiver in the presence of multipath interference has been shown and described. Varying the frequency of the transmission among a sequence of available frequencies over a time interval minimizes the impact of multipath effects in the received signals.

Absolute Positioning

Although the above disclosure has described the transmission of a single signal, albeit at varying frequencies, according to one aspect of the invention it is realized that when using a method for determining the position of an object with embedded transmit antennas, phase discrimination has practical limitations in precision of about one degree of difference in phase angles. This means that the achievable resolution of the position of an object will be limited to a precision of about 1/360 of a wavelength.

Therefore, to achieve high resolution, shorter wavelengths—i.e., higher frequency signals—must be used. However since the value of phase difference repeats with every wavelength of separation between transmit antenna and receiver, shorter wavelengths also lead to more positions of ambiguity within a given region of space.

Figure 17:
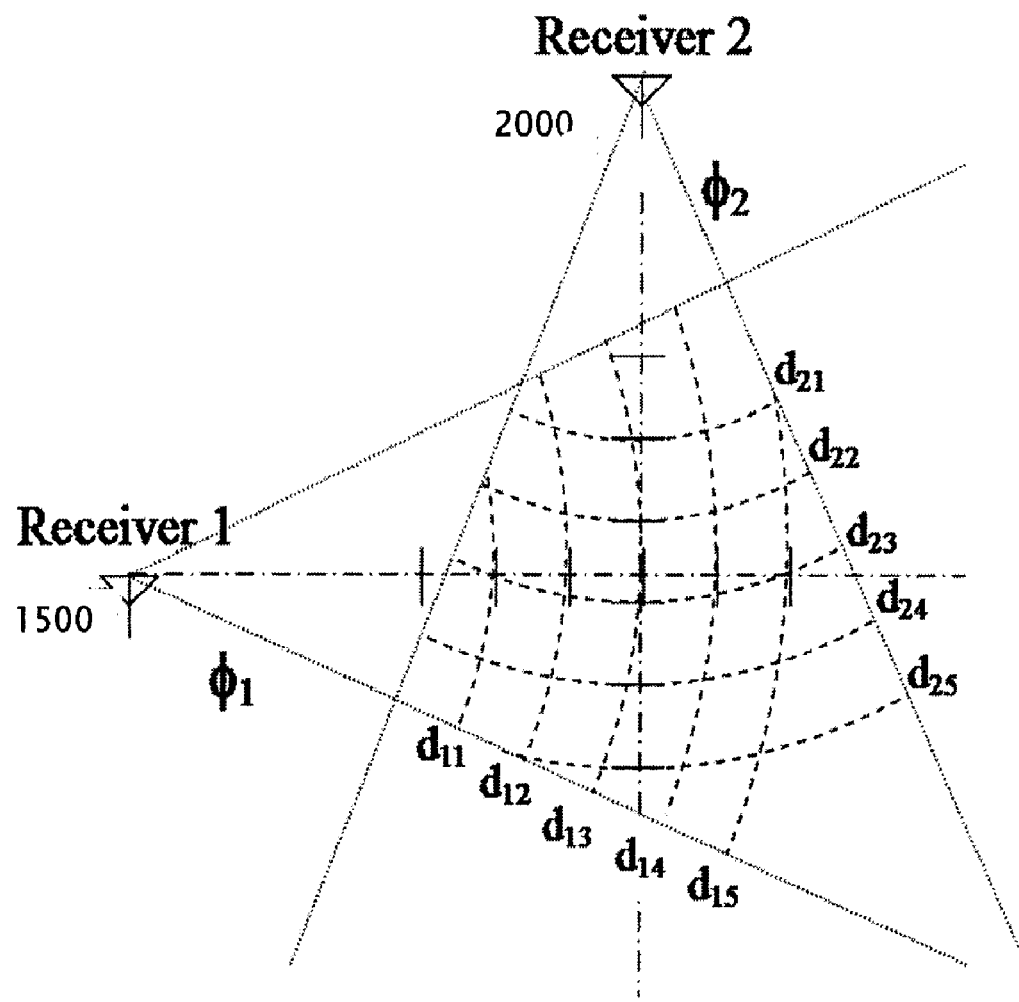
FIG. 17 illustrates phase ambiguity that may occur when transmitting high frequency signals.

FIG. 17 is a graph provided to illustrate the ambiguity that can arise when using shorter wavelengths. A first receiver 1500 detects a phase angle $\phi_1$ with respect to the reference signal. This can place the transmit antenna at any of the distances $d_{11}$, $d_{12}$, $d_{13}$, $d_{14}$, etc., from receiver 1500. A second receiver 2000 detects a phase angle $\phi_2$ with respect to the reference signal. This can place the transmit antenna at any of the distances $d_{21}$, $d_{22}$, $d_{23}$, $d_{24}$, etc., from receiver 2000. It can be seen that there are many possible positions for the transmit antenna for these two phase angles. It will be appreciated that even with a third receiver there will be many possible positions of the transmit antenna in three-dimensional space for a given set of phase angles. Additional receivers will narrow down the number of possibilities but not unambiguously identify the actual position of the transmit antenna.

The above problem is compounded in practical environments in which a transmit assembly may "drop out of sight" of a receiver for a short time, perhaps due to a person or object moving in the way or to interference generated by equipment in the vicinity.

However, according to one aspect of the invention it is realized that if it is possible to simultaneously transmit two RF signals of significantly different wavelengths from the same transmitting antenna, then the ambiguity can be reduced to the certainty inherent in the longer wave length, while the resolution of the position can be maintained by the precision of the shorter wavelength.

Figure 18:
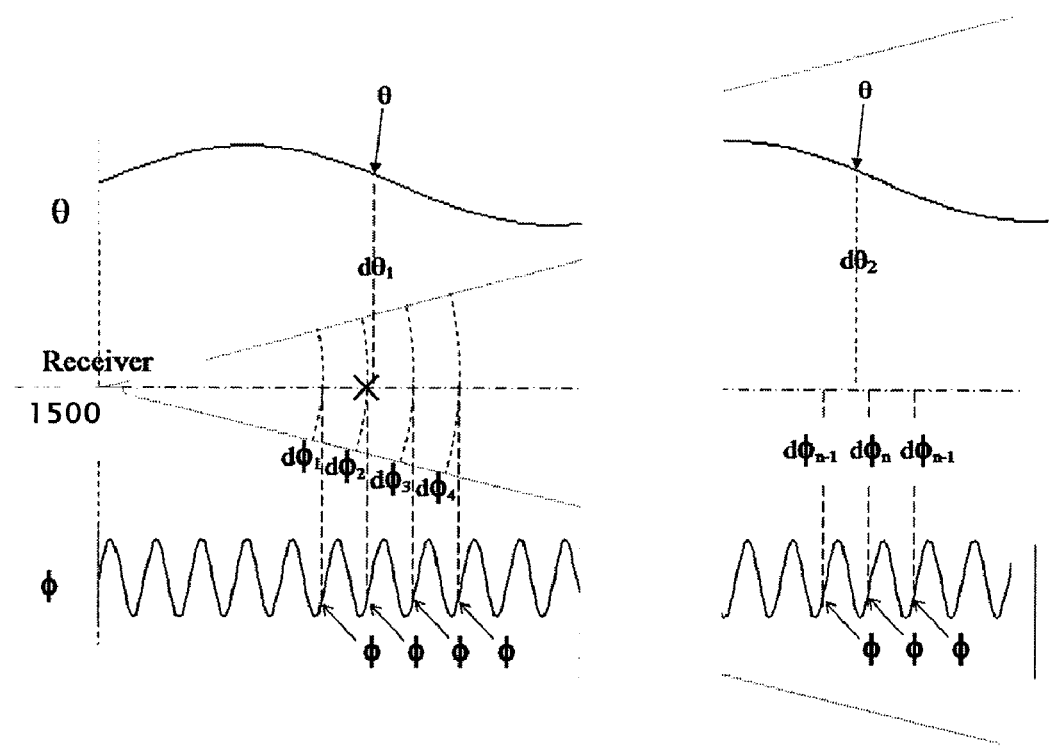
FIG. 18 includes diagrams of graphs that illustrate how long and short wavelengths can be used to resolve a position.

The simultaneous transmission of two frequencies is illustrated in FIG. 18, which shows the case of only one receiver 1500. In the example of FIG. 18, with appropriate filtering receiver 1500 may detect two signals transmitted by the transmit antenna and therefore two phase angles with respect to the previously established reference. Phase angle φ represents the angle detected for the high frequency (shorter wavelength) signal, and phase and θ represents the phase angle detected for the lower frequency (longer wavelength) signal. Phase angle φ makes it possible to position the transmit antenna at a multiplicity of distances $d_{φ1}$, $d_{φ2}$, $d_{φ3}$, $d_{φ4}$, etc., from receiver 1500. By contrast, phase angle θ makes it possible to position the transmit antenna at only two distances, $d_{θ1}$ or $d_{θ2}$ from the receiver 1500. However, the coarse precision of θ is sufficient to identify which of the possible precise distances indicated by φ represents the actual position of the object.

In the present invention, the transmit antenna transmits two frequencies at the same time, one with a sufficiently long wavelength to unambiguously determine the position of the object within the region of interest but to only a coarse degree of precision, and the other with a sufficiently short wavelength to determine the position of the object to the desired degree of position.

In one embodiment—for example, one suitable for a navigated medical environment—the two frequencies are approximately 100 MHz and 5.8 GHz, respectively. The table below shows two frequencies, 100 MHz and 5.868 GHz, along with their corresponding wavelengths. At 100 MHz, it is possible to resolve the position of an object to only a precision of about 8 mm, even using a highly accurate phase discriminator resolvable to one degree. By contrast, in the 5.8 GHz range, it is possible to resolve the position of an object to better than 1 mm, even with a phase discriminator capable of resolving to only within 5 degrees.

TABLE I

| FREQUENCY (MHz) | WAVELENGTH | PHASE DISCRIMINATOR | SINGLE FREQUENCY RESOLUTION | AMBIGUITY |
|---|---|---|---|---|
| 100 | 2997.92 | 1 | 8.33 | 1 |
| 5868 | 51.09 | 5 | 0.71 | 39 |

However, the 100 MHz signal can correctly determine the position of the object to a unique position within a cube that is 2 meters on a side. By contrast, there are about 39 different distances within a 2-meter cube that correspond to exactly the same phase difference for a signal of 5.868 GHz.

Figure 19:
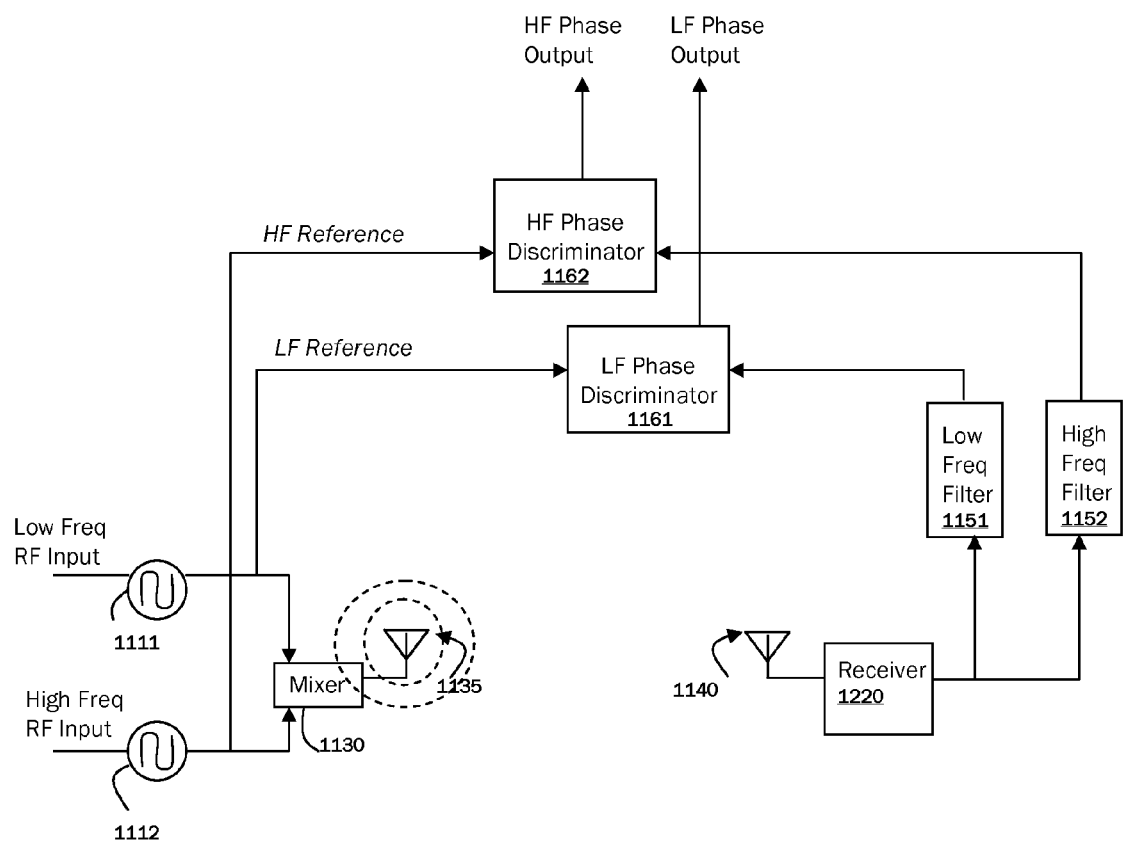
FIG. 19 illustrates one embodiment that may be used to provide a high and low frequency signals to receivers to determine a position with high resolution over a large area.

FIG. 19 illustrates such an embodiment. Input RF or microwave signals 1111 and 1112 are of lower and higher frequencies, respectively. These are applied to mixer 1120 and also to phase discriminators 1161 and 1162, where they act as reference signals. The two input RF signals are combined in mixer 1130 and applied to transmitting antenna 1135, for transmission to receiving antenna 1140. Receiving antenna 1140 is coupled to receiver 1141, which receives and amplifies the combined signal. This signal is then passed to filters 1151 and 1152 to extract the low and high frequency components, respectively. These component signals are then passed to phase discriminators 1161 and 1162, respectively, to derive phase differences 1171 and 1171 between the two received frequencies and their reference frequencies. Raw distances are calculated for each of these phase differences, and they are each included in a position determination process such as that illustrated in FIG. 7.

In practical situations, it is often difficult to transmit signals of radically different frequencies from the same antenna efficiently. Therefore, according to another aspect of the present invention, a refinement of the above method is provided to transmit two simultaneous signals of nearly the same wavelength and to derive the lower frequency signal from them. For example, if the two frequencies are 5.7 and 5.8 GHz and the phase relationship between them is fixed, then a 100 MHz signal can be derived from them, also with a fixed phase relationship.

Figure 20:
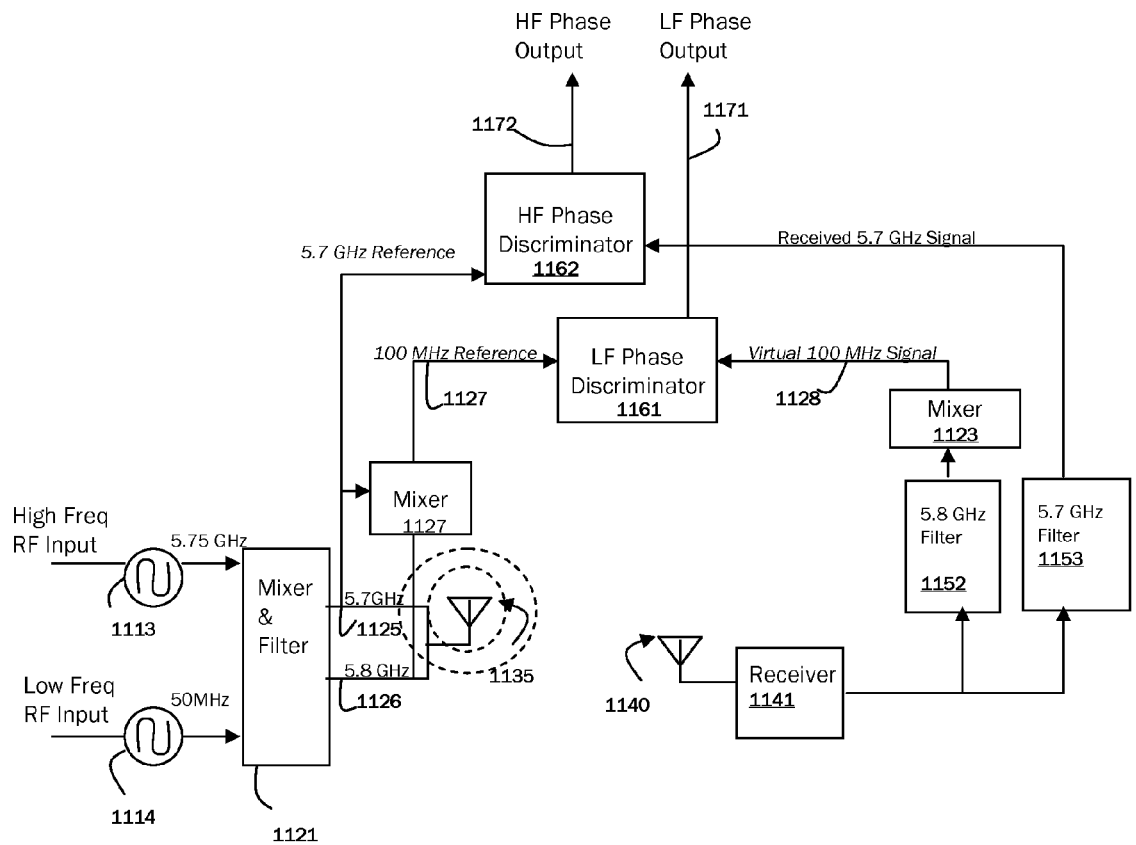
FIG. 20 illustrates a second embodiment of transmit circuitry that may be used to transmit two signals having different wavelengths, where the signals of FIG. 20 are phase locked to determine a position with high resolution in a large area.

FIG. 20 illustrates a preferred embodiment. An input 5.75 GHz signal 113 and a low frequency 50 MHz signal 1114 are coupled to mixer and filter 1121. The mixing of these two frequencies produce two sidebands frequencies, 5.7 GHz signal 1125 and 5.8 GHz signal 1126. Mixer and filter 1121 also filters out the original 5.75 GHz and 50 MHz signals leaving only the two sideband frequencies. The phase relationship between these sidebands is defined by the original 50 MHz signal. As a result, because the same source oscillator is used to create both of the signals that are input to the mixer, the resulting signals are phase locked and do not drift. As a result, the phase relationship between the signals is constant and permits reliable synthesizing of a 100 MHz signal whose phase angle can be used to determine a position within the necessary precision. In one embodiment the signal is referred to as a 'beat' signal, and is obtained by taking the difference between the 5.7 GHz and 5.8 GHz signals. It will be appreciated that if the 5.7 GHz and 5.8 GHz signals are not kept in fixed phase relationship, the 100 MHz difference between them which provides the basis for the beat signal is unusable for distance determination based on phase angles because the phase reference at the origin of the 100 MHz signal would not be constant.

Signals 1125 and 1126 are combined and sent to transmit antenna 1135. In addition they are sent mixer 1122, to synthesize a 100 MHz reference beat signal 1127 representing the difference between 5.7 GHz and 5.8 GHz 127 for reference to the low frequency phase discriminator 1161. Signal 1125 is also sent as reference to the high frequency phase discriminator 1162.

The transmit antenna transmits the combined 5.7 and 5.8 GHz signal to receiving antenna 1140 and receiver 1141. The combined received signal is then coupled to filters 1152 and 1153 to extract the component 5.7 GHz and 5.8 GHz signals. The 5.7 GHz signal is sent to the high frequency phase discriminator 162, to obtain the phase differences 1172 from the reference signals 1125.

In addition, the outputs of 5.7 GHz filter 153 and 5.8 GHz filter 152 are sent to mixer 1123 to synthesize a so-called 'virtual' 100 MHz beat signal 1128 representing the difference between 5.7 GHz and 5.8 GHz. The respective reference and virtual beat signals 1127 and 1128 are applied to phase discriminator 1161 to obtain the phase angle 1171 of the 100 MHz synthesized signals.

With such an arrangement, a low frequency signal is virtually transmitted between a transmit antenna and a receiver by transmitting two high frequency signal and determining the difference between the high frequency signals at the transmitter and at the receiver. Such an arrangement removes the need to provide high and low frequency antennas in the transmit antenna assembly. In addition, because the 100 MHZ signals are directly synthesized from the transmitted and received signal pairs, they retain the phase coherence relationship that enables them to be used to calculate position.

This phase difference can be used to position an object within one wavelength of a 5.7 GHz signal. It therefore makes it possible to reconstruct the position of an object that is temporarily obscured from some or all of the receiving antennas 1140 without having to recalibrate it. Since the actual transmitted signals of 5.7 GHz and 5.8 GHz are so close in wavelength, a single set of transmit and receive antennas can used to efficiently convey both course and fine position information.

It will be appreciated that there will be many other embodiments within the scope of this invention, some using analog methods and others using digital methods. In some embodiments, no low-frequency signal may be actually synthesized. Instead, the relative phases of the two high-frequency signals are used to determine a "virtual" phase angle for the low-frequency signal, both at calibration time and during each measurement of the changes in phase differences. All variations of these embodiments are within the scope of this invention.

Exemplary Embodiment

Thus various aspects of the present invention have been shown and described, each of which has stand alone utility in a navigated medical environment. As described above, receiver calibration is crucial to enabling precise object tracking and the method and system described with regards to FIGS. 9-11 facilitates calibration of a reference frame prior to each navigated procedure. The concept and application of confidence weights can be applied to distance calculations to mitigate the effects of interference and increase the tolerance of the navigated medical system through real time, intelligent analysis of signal and distance information within and across the receiver framework. Multi-path interference is minimized through the transmission of a signal having a pattern of unique frequencies, storage of prior distances to resolve to appropriate wavelengths and filtering of the results to ensure that the 'best' result is identified. In addition, it is realized that transmitting a signal using multiple frequencies can provide increased resolution and accuracy.

In an exemplary embodiment, a 5.7 and 5.8 GHz signal are generated using the same oscillator, as shown in FIG. 6, and mixed to provide a 100 MHz signal. The frequency of the 5.7 GHz signal is varied in a range over a sequence interval by transmitting a pattern of unique frequencies within the range to the receiving device. Each receiver receives the signal pattern for each frequency step and calculates an estimated distance for the frequency step using the methods described with regard to FIG. 14. The distance calculation and signal information may be used to determine a confidence weight to assign to the distance, either before or after filtering. The resulting distances are forwarded to a positioning algorithm, which uses information from the 100 Mhz wavelength to resolve to a wavelength and a minimization process such as that in FIG. 7 to resolve to a smaller granularity. Preferred embodiments of the invention advantageously incorporate the confidence weight concepts when determining distances in the presence of multipath interference, as described with regards to FIGS. 12-16. Multi-path interference and confidence weight calculations can further be used to improve results when using the absolute positioning methods and systems of FIGS. 16-20. With such an arrangement a navigated medical system with increased accuracy and reliability is provided.

It should be noted that although the above description of confidence weights, multi-path and absolute positioning have been has directed towards an embodiment where the object to be tracked is an instrument or anatomical marker, it is not required that the tracked object be the transmitting device and that the tracking object be a receiving device. It is envisioned that aspects of the invention may be readily adapted to an environment where a reference frame comprises transceivers which transmit to the object to be tracked, and distance and position calculations are made from that perspective. Thus the present invention is not limited to any particular transmission direction.

Having described various embodiments of the invention, it will be appreciated that many of the functions described above may be implemented as computer programs that can be delivered to a computer in many forms; including, but not limited to: (a) information permanently stored on non-writable storage media (e.g. read only memory devices within a computer such as ROM or CD-ROM disks readable by a computer I/O attachment); (b) information alterably stored on writable storage media (e.g. floppy disks and hard drives); or (c) information conveyed to a computer through communication media for example using baseband signaling or broadband signaling techniques, including carrier wave signaling techniques, such as over computer or telephone networks via a modem The above description and figures have included various process steps and components that are illustrative of operations that are performed by the present invention. However, although certain components and steps have been described, it is understood that the descriptions are representative only, other functional delineations or additional steps and components can be added by one of skill in the art, and thus the present invention should not be limited to the specific embodiments disclosed. In addition it is understood that the various representational elements may be implemented in hardware, software running on a computer, or a combination thereof.

While the invention is described through the above exemplary embodiments, it will be understood by those of ordinary skill in the art that modification to and variation of the illustrated embodiments may be made without departing from the inventive concepts herein disclosed. Accordingly, the invention should not be viewed as limited except by the scope and spirit of the appended claims.

The invention claimed is:

1. A method for determining a position of an object includes the steps of:
generating a confidence weight for association with a measured distance between the object and an antenna in response to historical data associated with the antenna; and
determining a position of the object by applying the confidence weight to the measured distance to control a degree of contribution of the measured distance in a determination of the position; and
using the determined position to track the object during a navigated procedure.

2. The method of claim 1 wherein the confidence weight is provided to increase a tolerance of a positioning system to one of signal interference and signal obstruction.

3. The method of claim 2 wherein the positioning system is a navigated medical system.

4. The method of claim 1 wherein the measured distance is determined in response to a signal transmitted between the object and the antenna, and wherein the confidence weight is further generated in response to a relationship between the signal and the historical data.

5. The method of claim 4 wherein the historical data includes at least one of historical data associated with the signal, historical data associated with the measured distance and historical data associated with the position.

6. The method of claim 5 wherein the historical data associated with the signal includes at least one of signal strength, signal phase and signal noisiness.

7. The method of claim 5 wherein historical data associated with the measured distance includes distance measurements for different frequencies of the signal.

8. The method of claim 5 wherein the historical data further includes historical data associated with one or more other receivers that are used to determine the position of the object.

9. The method of claim 4 wherein the confidence weight is determined in response to a trend of the historical data and one of the signal, the measured distance or the position.

10. The method of claim 4 wherein the confidence weight is determined in response to a divergence of one of the signal, the measured distance and the position from a trend of the historical data.

11. The method of claim 8 wherein the confidence weight is determined in response to a divergence of one of the signal, the measured distance and the position from a trend of historical data of the one or more other receivers.

12. The method of claim 4 wherein the measured distance is a raw distance determined in response to a phase of the signal.

13. The method of claim 4 wherein the signal is transmitted by a transmitter coupled to the object and received by a receiver coupled to the antenna.

14. The method of claim 4 wherein the signal is transmitted by a transmitter coupled to the antenna and received by the object.

15. A method of determining a position of an object includes the steps of, for each of a plurality of antennas:
  receiving a signal transmitted between the object and a respective antenna;
  generating a respective confidence weight to associate with a measured distance between the object and the respective antenna using historical information associated with at least one antenna of the plurality of antennas;
  comparing an estimated distance to each of the measured distances to generate a distance offset;
  applying the respective confidence weight to a function of the associated distance offset for each of the plurality of receivers to provide a plurality of weighted distance offsets;
  summing the weighted distance offsets and comparing a result to a threshold; and
  responsive to the distance offset exceeding the threshold, adjusting the estimated distance and repeating the steps of comparing, applying and summing until the result is less than or equal to the threshold.

16. A system for determining the position of an object comprising:
  a non-transitory computer readable medium having computer instructions stored therein, and coupled to a processor of the system to cause said processor to thereby perform said computer instructions;
  a historical data store stored on the computer readable medium and comprising historical information associated with an antenna;
  program code stored on the computer readable medium, for generating a confidence weight and associating the confidence weight with a measured distance between the antenna and the object; and
  program code stored on the computer readable medium for determining a position of the object including applying the confidence weight to the measured distance to control a degree of contribution of the measured distance to the position; and
  wherein processing units within the system operate on computer instructions in the program code for generating the confidence weight and the program code for determining a position to track the object during a navigated procedure.

17. The system of claim 16 wherein the confidence weight is provided to increase a tolerance of the system to one of signal interference and signal obstruction.

18. The system of claim 17 wherein the system is a navigated medical system.

19. The system of claim 16 wherein the measured distance is determined in response to a phase of a signal transmitted between the object, wherein the signal is transmitted at a plurality of frequencies and wherein the historical data includes historical data for each frequency of the plurality of frequencies.

20. A system for determining a position of an object includes:
  a signal generator for generating a signal for transmission between the object and a plurality of antennas in a frame of reference;
  means for determining and associating a plurality of confidence weights to a corresponding plurality of measured distances, each measured distance associated with one antenna of the plurality of antennas;
  positioning logic for determining a position of the object by:
    deriving an estimated distance to each of the plurality of antennas using an estimated position;
    calculating a distance offset for each antenna by comparing the measured distance of the associated antenna to the associated derived distance;
    applying the confidence weights to a function of corresponding distance offsets to provide a plurality of weighted distance offsets and summing the weighted distance offsets to provide a result; and
  responsive to the result being outside a threshold, adjusting the estimated position and repeating the steps of deriving, calculating and applying until the result is within the threshold.

* * * * *